United States Patent

Keyes et al.

[11] Patent Number: 6,139,924
[45] Date of Patent: Oct. 31, 2000

[54] CHIRAL LIQUID CRYSTAL COMPOUNDS HAVING A FLUORINATED TERMINAL PORTION

[75] Inventors: Michael P. Keyes, Minneapolis; Marc D. Radcliffe, Newport; Steven J. Martin, Shoreview; Daniel C. Snustad, Woodbury; Kenneth A. Epstein, St. Paul, all of Minn.

[73] Assignee: 3M Innovative Properties Company, St. Paul, Minn.

[21] Appl. No.: 09/196,848

[22] Filed: Nov. 20, 1998

[51] Int. Cl.$^7$ .......................... C09K 19/52; C09K 19/34; C07D 239/02; G02F 1/13
[52] U.S. Cl. ................ 428/1.1; 252/299.61; 252/299.01; 349/174; 349/171; 349/184; 544/303
[58] Field of Search ........................ 252/299.01, 299.61, 252/299.62, 299.63, 299.66; 349/174, 171; 428/1.1; 544/303

[56] References Cited

U.S. PATENT DOCUMENTS

| | | | |
|---|---|---|---|
| 2,519,983 | 8/1950 | Simons | 204/62 |
| 4,367,924 | 1/1983 | Clark et al. | 358/334 |
| 4,886,619 | 12/1989 | Janulis | 252/299.1 |
| 5,082,587 | 1/1992 | Janulis | 252/299.01 |
| 5,254,707 | 10/1993 | Strickler et al. | 556/413 |
| 5,262,082 | 11/1993 | Janulis et al. | 252/299.01 |
| 5,262,388 | 11/1993 | Munro et al. | 504/271 |
| 5,362,919 | 11/1994 | Costello et al. | 568/601 |
| 5,377,033 | 12/1994 | Radcliffe | 359/75 |
| 5,399,291 | 3/1995 | Janulis et al. | 252/299.01 |
| 5,399,701 | 3/1995 | Janulis | 546/298 |
| 5,417,883 | 5/1995 | Epstein et al. | 252/299.01 |
| 5,437,812 | 8/1995 | Janulis et al. | 252/299.01 |
| 5,474,705 | 12/1995 | Janulis et al. | 252/299.01 |
| 5,482,650 | 1/1996 | Janulis et al. | 252/299.01 |
| 5,631,752 | 5/1997 | Tanaka | 349/173 |
| 5,641,427 | 6/1997 | Shinjo et al. | 252/299.01 |
| 5,658,491 | 8/1997 | Kistner et al. | 252/299.01 |
| 5,702,637 | 12/1997 | Johnson et al. | 252/299.61 |
| 5,855,812 | 1/1999 | Radcliffe et al. | 252/299.01 |
| 5,928,562 | 7/1999 | Kistner et al. | 252/299.6 |
| 5,972,241 | 10/1999 | Johnson et al. | 252/299.61 |
| 6,030,547 | 2/2000 | Hasegawa et al. | 252/299.61 |
| 6,057,007 | 5/2000 | Amano et al. | 428/1.1 |

FOREIGN PATENT DOCUMENTS

| | | |
|---|---|---|
| 755 993 | 1/1997 | European Pat. Off. . |
| 769 542 | 4/1997 | European Pat. Off. . |
| 769 543 | 4/1997 | European Pat. Off. . |
| WO 91/00897 | 1/1991 | WIPO . |

OTHER PUBLICATIONS

Chandani et al., *Japan J. Of Appl. Physics* 27(5), pp. L–729–732, 1988.
Clark et al., *Appl Phys. Lett.* 36, p. 899, 1980.
Frick, *Synthese*, vol. 7, pp. 621–623, 1992.
Meyer et al., *J. Physique* 36, pp. 1–69, 1975.
Miyasato et al., *Jap. J. Appl. Phys.* 22, pp. 661, 1983.
Nohira et al., *Mol. Cryst. Liq. Cryst.*, 180B, pp. 379, 1990.
P.J. Collings et al., "Introduction of Liquid Crystals Chemicstry & Physics," *Taylor & Francis Ltd.*, pp. 271–285, 1997.
P.J. Collings, "Liquid Crystals: Nature's Delicate Phase of Matter," *Princeton University Press*, pp. 100–103, 1990.
Zaschke et al., "Synthese neidrigschmelzender Kristallin– Flussiger Heterocyclen; 5–n–Alkyl–2–[4–n–alkanoyloxy–phenyl]pyrimidine," *Z.Chem.* 15, pp. 441–443, 1975.

*Primary Examiner*—Shean C. Wu
*Attorney, Agent, or Firm*—Kent S. Kokko

[57] ABSTRACT

Novel liquid crystal compounds are provided which exhibit less temperature dependent switching properties, for the reliable and consistent operation of liquid crystal devices. The liquid crystal compounds comprise (a) an achiral fluorochemical terminal portion that comprises a terminal fluoroalkyl, fluoroether, perfluoroalkyl, or perfluoroether group; a chiral terminal portion comprising a saturated or unsaturated chiral hydrocarbon or chiral hydrocarbon ether group comprising a chiral center; and a central core connecting the terminal portions; said chiral terminal portion having at least three in-chain atoms (an "extended group") between said chiral center of the chiral terminal portion and said central core.

15 Claims, 3 Drawing Sheets

CHIRAL LIQUID CRYSTAL COMPOUNDS HAVING A FLUORINATED TERMINAL PORTION

FIELD OF THE INVENTION

This invention relates to fluorinated chiral smectic liquid crystal compounds, to liquid crystal compound mixtures and to electrooptical display devices containing such compounds.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available.

A recent advance in the liquid crystal art has been the utilization of tilted chiral smectic liquid crystals, one class of which are termed ferroelectric liquid crystals, in devices which give microsecond switching and bistable operation. Ferroelectric liquid crystals were discovered by R. B. Meyer et al. (J. Physique 36, 1–69 (1975).). A high speed optical switching phenomenon using a "surface-stabilized ferroelectric liquid crystal" (SSFLC) was discovered for the ferroelectric liquid crystals by N. A. Clark et al. (Appl. Phys. Lett. 36, 899 and U.S. Pat. No. 4,367,924).

Many new ferroelectric liquid crystals have been developed and their switching characteristics extensively tested. Although devices employing these materials exhibit high response speed and wide viewing angles, many problems remain in developing SSFLC devices. These problems have included insufficient threshold characteristics, unsatisfactory contrast (due to chevron defects), and insufficient bistability due to difficulties in controlling alignment.

More recently, antiferroelectric liquid crystals (AFLC), another class of tilted chiral smectic liquid crystals, have been developed. Antiferroelectric liquid crystals are switchable in a chiral smectic $C_A$ phase ($SC_A^*$ phase) in addition to the tilted chiral smectic C phase ($S_C^*$ phase) used in ferroelectric liquid crystal devices.

One of the most important characteristics of a liquid crystal display device is its response time, i.e., the time required for the device to switch from the on (light) state to the off (dark) state. Especially important for practical operation of larger devices is the response time with respect to temperature. In such devices, temperature non-uniformities may adversely effect the performance and require some form of compensation, unless the switching speed is largely independent of temperature. In a ferroelectric or anti-ferroelectric device, response time $\tau_{electric}$ is proportional to the rotational viscosity ($\eta$) of the liquid crystal compound(s) contained within the device and is inversely proportional to their polarization ($P_s$) and to the applied electric field (E) according to the following formula:

$$\tau_{electric} = \eta / P_s E.$$

Thus, response time can be reduced by using compound(s) having high polarizations or low viscosities, and such compounds are greatly desired in the art. In addition, compounds with polarizations that rapidly increase with decreasing temperature can lead to temperature independence or reduced temperature dependence of switching.

In the passive addressing of liquid crystal compounds exhibiting a spontaneous polarization, however, low polarization mixtures may be preferred for the practical operation of a liquid crystal device. Polarization reversal fields are larger for higher polarization mixtures, and polarization reversal fields cause switching or partial switching back to a material's original director alignment. This results in loss of the bistability that is crucial to the passive-matrix driving of ferroelectric liquid crystal devices.

Another potential disadvantage of using high polarization mixtures is the partial switching of their director alignment in response to non-switching (secondary) signals in a driving waveform. This continued response or fluctuation of the director causes a large decrease in the contrast ratio of a ferroelectric liquid crystal device.

There remains a need in the art for liquid crystal materials having fast response times, ideally possessing broad smectic temperature ranges to enable operation of the device over a broad range of temperatures, or should be capable of combination with other liquid crystal compounds having different smectic temperature ranges without adversely affecting the smectic phase behavior of the base mixture. There further remains a need in the art for materials which have low polarization values, and which can provide reduced temperature dependence of the response time. Further, there remains a need in the art for novel liquid crystal materials which exhibit tristable switching.

SUMMARY OF THE INVENTION

Briefly, in one aspect, this invention provides fluorine-containing, chiral liquid crystal compounds having smectic mesophases or latent smectic mesophases. (Compounds having latent smectic mesophases are those which by themselves do not exhibit a smectic mesophase, but which, when in admixture with compounds having smectic mesophases or with other compounds having latent smectic mesophases, develop smectic mesophases under appropriate conditions.)

The chiral liquid crystal compounds of the invention comprise (a) an achiral fluorochemical terminal portion which comprises a terminal fluoroalkyl, fluoroether, perfluoroalkyl, or perfluoroether group; (b) a chiral terminal portion comprising a saturated or unsaturated, chiral hydrocarbon or chiral hydrocarbon ether group comprising a chiral center; and (c) a central core connecting the terminal portions; the chiral terminal portion having at least three in-chain atoms (an "extended group") between said chiral center of the chiral terminal portion and the central core.

Surprisingly, in comparison with similar compounds having fewer than three in-chain atoms between a chiral center of the chiral terminal portion and the central core, the compounds of the invention provide comparable electrooptic response speeds in spite of their lower measured polarization values. These lower polarization values, in combination with broad mesogenic temperature ranges, enable the utilization of liquid crystal mixtures that contain up to 100% of the chiral (optically active) compounds of the invention. In general, mixtures containing a high concentration of the compounds of this invention exhibit less temperature dependent switching properties, which is important for the reliable and consistent operation of liquid crystal devices.

Furthermore, the use of high concentrations of liquid crystal compounds having low polarizations also provides a decrease (relative to the use of low concentrations of compounds having high polarizations) in the partial switching response of the resulting compositions to non-switching (secondary) signals in the driving waveform that is commonly used in the passive addressing of liquid crystal devices. Such a decrease in this response is critical for improving the contrast of a device.

In another aspect, this invention provides liquid crystal display devices utilizing both the liquid crystal compounds of the invention and mixtures containing the liquid crystal compounds of the invention. In yet another aspect, the invention provides liquid crystal compounds that exhibit tristable switching, and liquid crystal display devices of the invention that can provide tristable switching, gradation display (grey scale), threshold control, hysteresis control, and fast response times. The devices can be either passive or active matrix devices.

In yet another aspect, this invention provides a process for reducing the temperature dependence of the switching speed of a liquid crystal mixture by combining at least one liquid crystal compound of this invention with at least one other compound liquid crystal composition comprising at least one smectic or latent smectic liquid crystal compound having a temperature dependent switching with slope typically more negative than −0.02, preferably more negative than −0.03.

These and other features, aspects, and advantages of the present invention will become better understood with regard to the following description, examples and accompanying Figures.

DETAILED DESCRIPTION OF THE INVENTION

Figure 1:
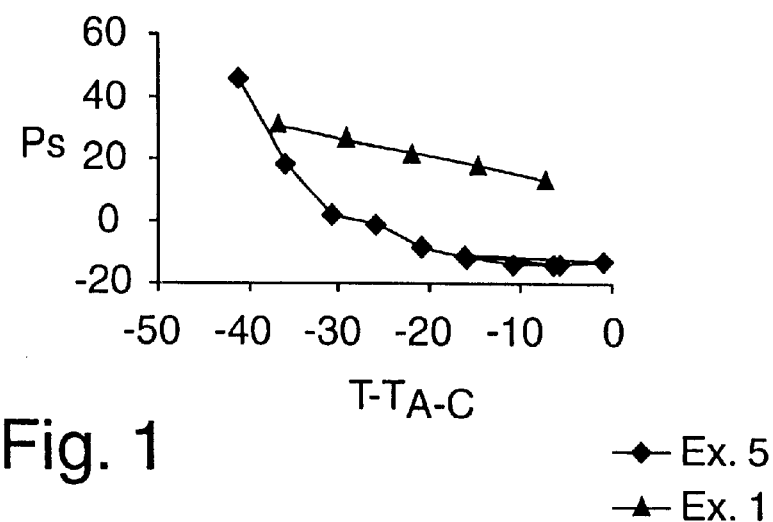
FIGS. 1 and 2 show the temperature dependence of the polarization ($P_s$) of the compounds of the invention.

The chiral terminal portion of the compounds of the invention can be represented by the formula —D—R*, where R* is a saturated or unsaturated, chiral hydrocarbon or hydrocarbon ether moiety containing at least one chiral center (asymmetric carbon atom); and D is non-directionally selected from the group consisting of a covalent bond, —C(=O)—O—$C_rH_{2r}$—, —O—$C_rH_{2r}$—, —O—(O=)C—$C_rH_{2r}$—, —C≡C—, —CH=CH—, —C(=O)—, —O(—$C_sH_{2s}$O—)$_tC_rH_{2r}$—, —$C_rH_{2r}$—, (—$C_sH_{2s}$O—)$_tC_rH_{2r}$—, —O—, —S—, —OSO$_2$—, —SO$_2$—, —SO$_2$—$C_rH_{2r}$—, —$C_rH_{2r}$—N—SO$_2$—,

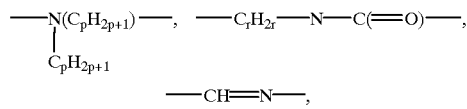

—CH=N—,

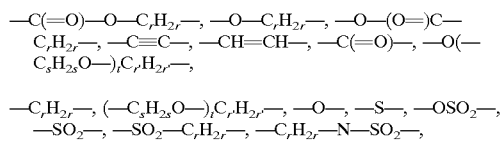

and combinations thereof, and where r and r' are independently integers of 0 to about 20, s is independently an integer of 1 to about 10 for each ($C_sH_{2s}$O), t is an integer of 1 to about 6, and p is an integer of 0 to about 4; with the proviso that at least one chiral center of R* is spaced from the central core by at least 3 in-chain atoms. Preferably D of —D—R* is —O—$C_rH_{2r}$— or —$C_rH_{2r}$—.

The achiral fluorochemical terminal portion of the compounds of the invention can be represented by the formula —D—$R_f$, where D is as previously defined and where $R_f$ is an achiral fluoroalkyl, perfluoroalkyl, fluoroether, or perfluoroether group. Preferably, $R_f$ is perfluoroalkyl or perfluoroether; more preferably, $R_f$ is perfluoroether, as the perfluoroether-containing compounds of the invention exhibit, e.g., a broad smectic C mesophase, good compatibility with other smectic C compounds, and advantageous layer spacing behavior. When the $R_f$ group of the fluorochemical terminal portion is perfluoroalkyl or perfluoroether, it can contain small amounts of residual carbon-bonded hydrogen atoms but is preferably completely fluorinated. Preferably D of —D—$R_f$ is —O—$C_rH_{2r}$—, —O(—$C_sH_{2s}$O—)$_tC_rH_{2r}$—, —$C_rH_{2r}$—, or (—$C_sH_{2s}$O—)$_tC_rH_{2r}$—.

In general, the compounds of this invention have a central core comprised of at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC=N—, —CH=CH—, —C≡C—, and —COSe—. The rings can be fused or non-fused. The heteroatoms within the heteroaromatic rings comprise at least one atom selected from the group consisting of nitrogen, oxygen, and sulfur. Non-adjacent ring carbon atoms in the alicyclic rings can be substituted by nitrogen, oxygen, or sulfur atoms. When the ring(s) are aromatic, heteroaromatic, substituted aromatic, or substituted heteroaromatic, the non-fused rings of the core are preferably no more than about two in number.

The chiral liquid crystal compounds of the invention exhibit exceptionally wide mesomorphic temperature ranges. When used in electrooptical devices, the compounds provide fast response times upon application of an electric field over broad temperature ranges. This makes them extremely useful in the preparation of mixtures that can operate in their active mesomorphic phase from around −30° C. to around 70° C.

A class of the above-described liquid crystal compounds of the present invention can be represented by the general formula I:

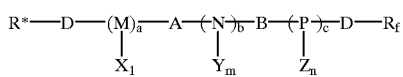
(I)

where M, N, and P are each independently selected from the group consisting of

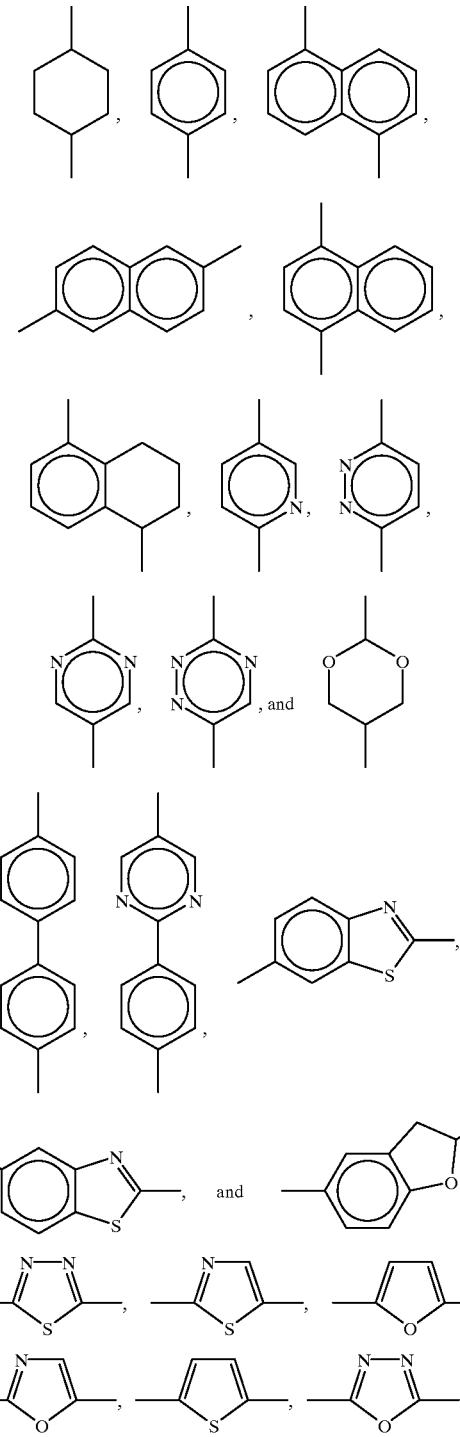

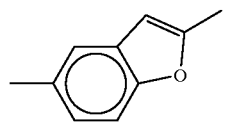

a, b, and c are each independently zero or an integer of from 1 to 3, with the proviso that the sum of a+b+c be at least 1 (and preferably no greater than 2);

each A and B are non-directionally and independently selected from the group consisting of a covalent bond, —C(=O)—O—, —C(=O)—S—, —C(=O)—Se—, —C(=O)—Te—, —(CH$_2$CH$_2$)k— where k is 1 to 4,

—CH=CH—, —C≡C—, —CH=N—, —CH$_2$—O—, —C(=O)—, and

—O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

each D is non-directionally and independently selected from the group consisting of a covalent bond, —C(=O)—O—C$_r$H$_{2r}$—, —O—C$_r$H$_{2r}$—, —O—(O=C—C$_r$H$_{2r}$—, —C≡C—, —CH=CH—, —C(=O)—, —O(—C$_s$H$_{2s}$O—)$_t$C$_r$H$_{2r}$—, —C$_r$H$_{2r}$—, (—C$_s$H$_{2s}$O—)$_t$C$_r$H$_{2r}$—, —O—, —S—, —C$_r$H$_{2r}$—N(C$_p$H$_{2p+1}$)—SO$_2$—,  —N(C$_p$H$_{2p+1}$)—, —OSO$_2$—,  —SO$_2$—,  —SO$_2$—C$_r$H$_{2r}$—, —OSO$_2$—, —SO$_2$—, —SO$_2$—C$_r$H$_{2r}$—, —C$_r$H$_{2r}$—N(C$_p$H$_{2p+1}$)—C—(=O)—, —CH=N—, and combinations thereof, where one or more hydrogen atoms can optionally be replaced with fluorine, and where r and r' are independently integers of 0 to about 20, s is independently an integer of 1 to about 10 for each (C$_s$H$_{2s}$O), t is an integer of 1 to about 6, and p is an integer of 0 to about 4;

R* is a chiral hydrocarbon or hydrocarbon ether moiety containing at least one chiral center (asymmetric carbon atom) with the proviso that at least one chiral center of R* is spaced from the central core by at least 3 in-chain atoms; R$_f$ is fluoroalkyl, perfluoroalkyl, fluoroether, or perfluoroether, preferably perfluoroalkyl or perfluoroether. More preferably, R$_f$ is perfluoroether.

In defining R$_f$, particularly preferred perfluoroalkyl groups are those which can be represented by the formula —$C_qF_{2q}X'$, where q is an integer of 1 to about 20 (and, preferably, is at least about 5) and X' is hydrogen or fluorine. Particularly preferred perfluoroether groups are those which can be represented by the formula—$(C_xF_{2x}O)_zC_yF_{2y+1}$, where x is independently an integer of 1 to about 12 for each $(C_xF_{2x}O)$, y is an integer of 1 to about 12, and z is an integer of 1 to about 10. Preferably, the perfluoroether group is linear, x is independently an integer of 1 to about 6 for each $(C_xF_{2x}O)$, y is an integer of 1 to about 6, and z is an integer of 1 to about 6.

A preferred subclass of the above-described chiral compounds of the invention can be represented by the formula:

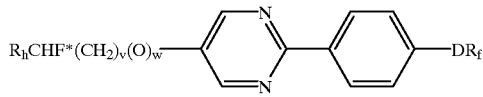

where D and $R_f$ are as previously defined, $R_h$ is a linear or branched alkyl group of 1 to about 10 carbon atoms, —CHF*— represents a chiral center of either (S) or (R) configuration, v is an integer from 2 to about 10, w is an integer of 0 or 1, with the proviso that v+w is at least 3, where one or more non-adjacent —$CH_2$— groups can be replaced by an oxygen atom and where one or more ring hydrogen atoms can be replaced by fluorine atoms.

Another preferred subclass of the above-described extended chiral compounds of the invention may represented by the formula:

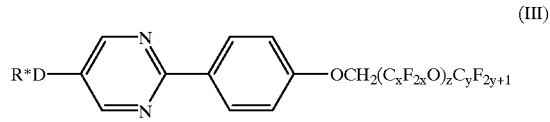

(III)

where R*, D, x, y and z are as previously defined, and where one or more ring hydrogen atoms may be replaced by fluorine atoms.

Surprisingly, many of the chiral liquid crystal compounds of Formula III have been found to exhibit tristable switching properties, making them useful as liquid crystal materials in both passive and active-matrix tristable devices having tristable switching, gradation display (grey scale), threshold control, hysteresis control, and fast response times.

Devices employing antiferroelectric liquid crystals (AFLC) have been described by Chandani et. al (Japan J. of Applied Physics 27(5), L729–732 (1988).). Antiferroelectric liquid crystals used in these devices exhibit three stable states: two stable states under the influence of an electric field and a third antiferroelectric state in the absence of an electric field. Antiferroelectric liquid crystals are characterized by having a distinct threshold and a double hysteresis that allows for a memory effect in either of the driven states. Antiferroelectric liquid crystals can be easily switched and provide devices that have few defects and that allow for the recovery of alignment.

In an AFLC device, with no applied electric field, an AFLC composition has a layered structure comprising many smectic layers, with the molecules of each layer being tilted in a direction opposite to those of the adjacent layer such that the liquid crystal composition has no net polarization. The alternating molecular director also results in a uniform optical axis parallel to the layer normal of the smectic layers. When placed between a pair of crossed polarizers such that one of the polarization axes of the polarizers is aligned with the uniform optical axis of the composition, the device exhibits a dark state. When an electric field is applied, the liquid crystal orients to align the spontaneous polarization with the electric field, resulting in one of two bright states, depending on the polarity of the electric field. Tristable switching behavior has also been observed for twisted ferroelectric and deformed helix devices.

The tristable liquid crystal display device of the invention comprises (a) first and second opposed substrates, at least one bearing an alignment coating and each bearing at least one electrode so as to define one or a plurality of pixels; (b) a tilted smectic or induced tilted smectic liquid crystal composition comprising at least one compound of Formula III disposed between the substrates; and (c) a pair of orthogonally disposed polarizers, each having a polarization (or light transmission) axis, one polarization axis being aligned with the zero field optical axis of a tilted smectic or induced tilted smectic mesophase of the liquid crystal composition; wherein the substrates are disposed so as to provide an alignment of the liquid crystal composition.

The substrates can comprise any of the materials known in the art to be useful as substrates for liquid crystal display devices, e.g., glass or plastic. The electrodes can be of any electrically conductive material, e.g., indium tin oxide (ITO), and can be applied to the surface of the substrates by any of the methods known in the art. Thus, the substrates can be coated with a film of $SnO_2$, $InO_3$, or ITO to form electrodes.

The substrates and the electrodes bear alignment coatings, which can comprise any of the useful alignment compositions known in the art. The two coatings can be the same or different. Materials suitable for use in preparing alignment coatings include polyvinyl alcohol, polyimide, polyamide-imide, polyester, polyamide, polyester-imide, polyparaxylylene, polycarbonate, polyvinyl acetal, polyvinyl chloride, polystyrene, polysiloxane, cellulose resin, melamine resin, urea resin, acrylic resin, and the like, and mixtures thereof. The surface of the alignment coatings can be subjected to a prescribed (uniaxial) alignment treatment as desired, for example, by rubbing the surface with a fibrous material such as velvet, cloth, or paper.

Substrates can be subjected to different alignment treatments in order to appropriately control an alignment state, particularly an initial alignment state. For example, one of the substrates can be provided with a rubbing-treated alignment coating, and the other can be provided with an alignment coating that is not subjected to rubbing and/or that comprises a composition that is different from that of the rubbing-treated alignment coating.

The liquid crystal display device of the invention preferably has at least one alignment coating of sufficient thickness to optimize the tristable switching properties of the device. The coating preferably has a thickness of from about 50 to about 5000 angstroms, more preferably from about 50 to about 2500 angstroms, in order to provide good driving characteristics, high reliability, and driving stability in a wide temperature range.

Preferably, one of the alignment coatings of the device of the invention comprises a polyimide or polyamide (e.g., nylon) film. The film can generally be prepared by applying a polyamic acid (polyimide precursor) or polyamide solution to the surface of the substrate, heating the applied coating layer, and then subjecting the resulting alignment coating to a rubbing treatment. If desired, the device of the invention can utilize alignment treatments such as those described, e.g, in EP 755993 (Canon) and U.S. Pat. No. 5,377,033 (Radcliffe), the descriptions of which are incorporated herein by reference. The device of the invention can optionally further comprise an insulating layer.

Substrates bearing said alignment coatings are separated by spacers at a fixed distance (the "cell gap") that, along with the alignment coatings, allows for the alignment of a liquid crystal composition that is contained in the resulting space between the substrates. The cell gap can generally be up to about 10 $\mu$, preferably from about 0.5 to about 5 $\mu$, in order for the device to exhibit tristable switching.

On the outer surfaces of substrates are affixed orthogonally disposed polarizers, each having a polarization (or light transmission) axis. The polarizers can be of any design and material known in the art to be useful in liquid crystal display devices. The polarization axis of one of the polarizers is aligned with the zero field optical axis of a tilted or induced tilted smectic mesophase of the liquid crystal composition.

The device of the invention containing the above-described liquid crystal composition can be driven by either a passive or an active matrix display. A typical liquid crystal display consists, e.g., of two polarizers, two transparent substrates, switching elements or electrodes to define pixels, and driver Integrated Circuits (ICs) to address rows and columns of pixels. The rows and columns can be constructed out of strips of conductive material.

In a passive matrix display, pixel-matrix elements can be defined by the intersection areas of rows and columns of a transparent conductor material, e.g., indium tin oxide (ITO), on the inner surfaces of two opposed substrates. To switch or address a liquid crystal composition disposed between these pixel-matrix elements, charge is applied to the appropriate row and column in order to change the orientation of the liquid crystal material (i.e., to change from a dark pixel to a bright pixel). Passive matrix displays have been described, for example, by Peter J. Collings in *Liquid Crystals: Nature's Delicate Phase of Matter*, pp. 100–103, Princeton University Press, Princeton, N.J. (1990) and by Peter J. Collings and Michael Hird in *Introduction to Liquid Crystals Chemistry and Physics*, pp. 271–285, Taylor and Francis Ltd., London (1997).

In order to improve on the limitations of passive matrix displays (such as crosstalk caused by driving waveforms), active matrix displays have been developed in the art. Active matrix displays typically have thin film transistors (TFTs) or diode arrays on a glass substrate, which address each pixel element. The TFT can comprise amorphous silicon ($\alpha$-Si) or polycrystalline silicon (p-Si) or can comprise a single crystal semiconductor device such as a CMOS (Complementary Metal Oxide Semiconductor) silicon-based device. The TFT electrically isolates one pixel element from the others in the display and eliminates the problem of partially active pixels. TFT can simply be considered a switch; when selected (on), it allows charge to flow through it, and, when off, it acts as a barrier that prevents or at least restricts the flow of charge. When a row of TFTs is addressed, gate lines are active, and the "switch" is turned on, allowing charge to flow from the columns into the pixels and to set the image for the frame cycle. Once a row has been addressed, the gate line is reverse biased (the switch is turned off) to insure that no charge can pass from the columns into the pixel elements. Thus, the pixel is now isolated as the rest of the display is addressed. Active matrix arrays have been described, for example, by Collings supra and in U.S. Pat. No. 5,631,752 (Tonaka), the descriptions of which are incorporated herein by reference.

The fluorine-containing liquid crystal compounds of the invention can be prepared by a process comprising the steps of (a) mixing at least one compound represented by the formula

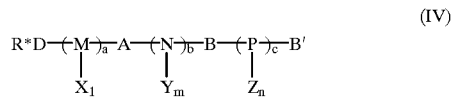
(IV)

with at least one compound represented by the formula $$B''—D—R_f \qquad (V)$$

or mixing at least one compound represented by the formula

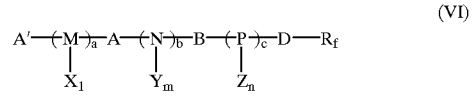
(VI)

with at least one compound represented by the formula $$R^*—D—A'' \qquad (VII)$$

or mixing at least one compound represented by the formula

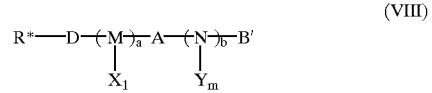
(VIII)

with at least one compound represented by the formula

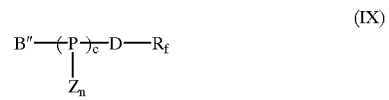
(IX)

where M, N, P, a, b, c, A, B, X, Y, Z, l, m, n, D, R*, and $R_f$ are as defined above for formula I; x is an integer of 0 or 1; and each A', A", B', and B" are independently selected from the group consisting of —H, —Cl, —Br, —I, —OH, —COOH, —CH(CH$_2$OH)$_2$, —SH, —SeH, —TeH, —NH$_2$, —COCl, —CHO, —OSO$_2$R$_f'''$, —OSO$_2$CH$_3$, —C≡CH, dialkyl borane, —CH═CH$_2$, —NH(C═O)OC$_q$H$_{2q+1}$, —NCO, —OSO$_2$-cyclo(C$_6$H$_4$)—CH$_3$, —CH$_2$COOH, and —CH(C(O)O—C$_q$H$_{2q+1}$)$_2$, where R$_f'''$ is a perfluoroalkyl group having from 1 to about 10 carbon atoms and q is an integer of 0 to about 20, and with the proviso that R*—D—A" can enter into an addition or condensation reaction with A' and that B"—D—R$_f$ can enter into an addition or condensation reaction with B';
and (b) allowing compounds IV and V, compounds VI and VII, or compounds VIII and IX to react, optionally in the presence of suitable coupling agent(s), i.e., reagent(s) which effect coupling. For Formula VII A" is preferably —OH (more preferably —CH═CH$_2$), and —D—R$_f$ is preferably —OCH$_2$—R$_f$.

The compounds of the invention are useful in admixture with themselves or with other chiral or achiral liquid crystal compounds (as dopants or as the major components), for electrooptical display applications. The compounds have a number of desirable properties when used in admixture with themselves or with other liquid crystal compounds, preferably compounds having fluorinated terminal portions such as those compounds disclosed, for example, in U.S. Pat. No. 4,886,619 (Janulis), U.S. Pat. No. 5,082,587 (Janulis), U.S. Pat. No. 5,254,707 (Janulis), U.S. Pat. No. 5,262,082 (Janulis et al.), U.S. Pat. No. 5,377,033 (Radcliffe), U.S. Pat. No. 5,399,291 (Janulis et al.), U.S. Pat. No. 5,399,701 (Janulis), U.S. Pat. No. 5,437,812 (Janulis et al.), U.S. Pat. No. 5,474,705 (Janulis et al.). U.S. Pat. No. 5,482,650 (Janulis et al.) U.S. Pat. No. 5,658,491 (Kistner et al.), U.S. Pat. No. 5,702,637 (Johnson et al.), and U.S. Ser. No. 08/998,400 filed Dec. 24, 1997 (Attorney's docket number 53589U.S.A.5A).

For example, the compounds of the invention when admixed with such preferred liquid crystal compounds show excellent compatibility, show a beneficial effect or only a minimal negative effect on the smectic C temperature range of the resulting mixtures (even when present at high concentrations), and provide tilted smectic mixtures (ferroelectric, antiferroelectric, or twist) having fast electrical response times. Mixtures containing the compounds exhibit favorable alignment, switching, response to an electric field, temperature dependence of response speed, temperature dependence of polarization, contrast, layer structure, and mesomorphic temperature ranges. Compounds of the invention can also be used to optimize mixture properties such as tilt angle, memory angle, spontaneous polarization and its temperature dependence, liquid crystal temperature range, switching behavior, birefringence, and the temperature dependence of layer spacing.

Most of the compounds of the present invention have enhanced smectic mesophases. Mixtures of the compounds of the invention with other liquid crystal materials can be formulated to provide desired transition temperatures and broad mesophase temperature ranges. Such mixtures preferably contain compounds having fluorinated terminal portions, such as those compounds described, for example, in U.S. Pat. No. 4,886,619 (Janulis), U.S. Pat. No. 5,082,587 (Janulis), and, most preferably, U.S. Pat. No. 5,262,082 (Janulis et al.), the descriptions of which are incorporated herein by reference. The liquid crystal compounds of the invention can also be used to prepare ferroelectric liquid crystal devices such as, e.g., those described in U.S. Pat. No. 5,377,033 (Radcliffe), U.S. Pat. No. 5,417,883 (Epstein et al.) and U.S. Pat. No. 5,641,427 (Shinjo) and in EP 769542 and EP 769543, the descriptions of which are incorporated herein by reference.

The compounds of this invention in admixture with other chiral or achiral liquid crystal compounds may exhibit chiral smectic liquid crystal behavior. Furthermore, many of the perfluoroether group-containing liquid crystal compounds of the invention when used alone or when mixed with other liquid crystal compounds of the invention or with achiral, fluorine-containing liquid crystal compounds (preferably, the perfluoroether group-containing liquid crystal compounds described in U.S. Pat. No. 5,262,082 (Janulis et al.)) exhibit a reduced temperature dependence of the smectic interlayer spacing. This property enables the spontaneous generation of a bookshelf type layer structure, which is ideal for a tilted smectic liquid crystal device. In general, the compounds of the invention exhibit maintenance or expansion of the smectic C layer spacing with decreasing temperature.

In the process of this invention, liquid crystal mixtures can be obtained having reduced temperature dependence of switching. With many liquid crystal mixtures, the switching speed, $\tau_{electric}$ increases with decreasing temperature, resulting in unacceptably slow switching speeds at operating temperatures of a device containing the liquid crystal mixture. Frequently, liquid crystal compounds having either high polarization ($P_s$) or low rotational viscosity ($\eta$) are added to a mixture in order to reduce the response time, but such methods do not reduce the temperature dependence of the response time.

The present invention provides a process for reducing the temperature dependence of the response time of a liquid crystal mixture, which comprises the step of combining:

(a) at least one compound of the invention which comprises (i) an achiral fluorochemical terminal portion which comprises a terminal fluoroalkyl, fluoroether, perfluoroalkyl, or perfluoroether group; (ii) a chiral terminal portion comprising a saturated or unsaturated chiral hydrocarbon or chiral hydrocarbon ether group comprising a chiral center; and (iii) a central core connecting the terminal portions; the chiral terminal portion having at least three in-chain atoms between the chiral center and the central core; with (b) a liquid crystal composition comprising at least one smectic or latent smectic liquid crystal compound exhibiting temperature dependent switching (when placed in a device)).

The compound(s) of composition (b), typically exhibit a plot of ln $\tau_{electric}$ vs. temperature, having a slope (the change of ln (natural log) of $\tau_{electric}$ with ΔT) typically more negative than −0.02, preferably more negative than −0.03. Especially suitable compounds for use in component (b) are fluorine containing, smectic or latent smectic liquid crystal compounds (preferably compounds having fluorinated terminal portions such as those compounds described, for example, in U.S. Pat. No. 4,886,619 (Janulis), U.S. Pat. No. 5,082,587 (Janulis), U.S. Pat. No. 5,254,707 (Janulis), U.S. Pat. No. 5,262,082 (Janulis et al.), U.S. Pat. No. 5,377,033 (Radcliffe), U.S. Pat. No. 5,399,291 (Janulis et al.), U.S. Pat. No. 5,399,701 (Janulis), U.S. Pat. No. 5,437,812 (Janulis et al.), U.S. Pat. No. 5,474,705 (Janulis et al.). U.S. Pat. No. 5,482,650 (Janulis et al.) U.S. Pat. No. 5,658,491 (Kistner et al.), U.S. Pat. No. 5,702,637 (Johnson et al.), and U.S. Ser. No. 08/998,400 filed Dec. 24, 1997 (Attorney's docket number 53589U.S.A.5A),the descriptions of which are incorporated herein by reference.

The process of the invention can be carried out by combining components (a) and b). The combining or mixing of the components can be effected by introducing the components to a vessel, generally with simultaneous and or subsequent agitation or stirring, e.g., roller mixing. The vessel can be either an open or a closed vessel of a size which is sufficient to hold both compositions while allowing room for mixing. The components can be formed prior to combination with each other, or alternatively, one of more of the compounds of either can be combined with one or more of the compounds of the other prior to addition of the remaining compounds. Any order and manner of combination of the compounds of the two components is acceptable. The resulting combination is preferably agitated or stirred sufficiently so that a homogeneous mixture is achieved. This is preferably facilitated by applying sufficient heat to melt the combination, or by dissolving the combination in a solvent, e.g., a polar aprotic solvent, with subsequent solvent removal, e.g., by evaporation.

These components (a) and (b) are mixed in ratios so as to balance or counteract the large negative slope of component (b) with the less negative or positive-tending slope of component (a). The liquid crystal compounds to be utilized in the process can be selected based upon the sign and magnitude of the $\Delta(\ln \tau_{electric})/\Delta T$ slope (or, in the case of latent smectic liquid crystal compounds, the sign and magnitude of the slope of mixtures containing the latent compounds(s), which can be determined by measuring the switching speed $\tau_{electric}$ at the desired temperatures as described below in the Examples. In general, composition (b) (generally having a more negative $\tau_{electric}$ slope than −0.02) can be combined with composition (a) (generally having a less negative $\tau_{electric}$ slope than −0.03 to −0.02 or even positive $\tau_{electric}$ slope) to obtain a combination having a desired intermediate (ln $\tau_{electric}$)/$\Delta T$ slope associated with a reduced temperature dependency of the switching speed.

Preferably, component (a) is utilized in amounts such that the resulting combination has a tau slope between −0.03 and 0.04 (more preferably, between −0.02 and 0.02; most preferably, between −0.01 and 0.01). However, in some cases a tau slope outside of these ranges may be desirable for a particular purpose and can be achieved through an iterative process of combining components (a) and (b) in varying ratios and measuring the net tau slope of the resulting combinations.

Another advantage of using the materials of this invention in the formulation of liquid crystal mixtures is the low birefringence which can be obtained. The low birefringence of the liquid crystal compounds of the invention (relative to their non-fluorine-containing analogues) allows the fabrication of devices with larger device spacings. Light transmission through, e.g., a surface-stabilized ferroelectric device (as described in U.S. Pat. No. 4,367,924 (Clark et al.) and U.S. Pat. No. 5,377,033 (Radcliffe) the descriptions of which are incorporated herein by reference) with two polarizers is represented by the following equation:

$$I=I_o(\sin^2(4\Theta))(\sin^2(\pi\Delta nd/\lambda))$$

where $I_o$=transmission through parallel polarizers
$\Theta$=material tilt angle
$\Delta n$=liquid crystal birefringence
d=device spacing
$\lambda$=wavelength of light used To maximize the transmission in a bistable device, both $\sin^2(4\Theta)$ and $\sin^2(\pi\Delta nd/\lambda)$ must be at maximum. This occurs when each term equals one. The first term is a maximum when the tilt angle equals 22.5°. This is a function of the liquid crystal and is constant for a given material at a given temperature. The second term is maximum when $\Delta nd=\lambda/2$. This demonstrates the importance of the low birefringence of the materials of this invention. Low birefringence allows a larger device thickness, d, for a given wavelength of light. Thus, a larger device spacing is possible while still maximizing transmission, allowing easier device construction.

For a tristable device the following equation is used:

$$I=I_o(\sin^2(2\Theta))(\sin^2(\pi\Delta nd/\lambda))$$

To maximize the transmission in a tristable device, both $\sin^2(2\Theta)$ and $\sin^2(\pi\Delta nd/\lambda)$ must be at maximum. This occurs when each term equals one. The first term is a maximum when the tilt angle equals 45°.

Objects and advantages of this invention are further illustrated by the following examples, but the particular materials and amounts thereof recited in these examples, as well as other conditions and details, should not be construed to unduly limit this invention.

EXAMPLES

In the following examples, all temperatures are in degrees Celsius and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn, were caused to react together to yield the chiral, fluorine-containing liquid crystal compounds of this invention.

Compounds prepared in the various examples of this invention were characterized by their melting or boiling point, and structures were confirmed by using at least one of the following methods of analysis: chromatography; $^{13}$C-, $^{1}$H-, and $^{19}$F-NMR; and infrared and mass spectroscopies.

The 5-alkyl-2-(4-hydroxyphenyl)pyrimidines used in the examples were prepared essentially as described by Zaschke and Stolle in "Synthese niedrigschmelzender Kristallin-Flussiger Heterocyclen; 5-n-Alkyl-2-[4-n-alkanoyloxy-phenyl]pyrimidine," Z.Chem. 15, 441–3 (1975). (S)- and (R)-2-fluoro-decyl-p-toluenesulfonate were prepared essentially as described by Nohira et al. in Mol. Cryst. Liq. Cryst. 180B, 379 (1990). Fluorinated alcohols were prepared essentially as described in U.S. Pat. No. 5,262,082 (Janulis et al.; the description of which is incorporated herein by reference) by sodium borohydride reduction of the corresponding perfluorinated acids (or derivatives), which had been prepared by electrochemical fluorination (ECF) or by direct fluorination (using elemental fluorine) of the corresponding hydrocarbon acids (or derivatives). See, e.g., the description of ECF given in U.S. Pat. No. 2,519,983 (Simons), the description of which is incorporated herein by reference. Direct fluorination is described, e.g., in U.S. Pat. No. 5,362,919 (Costello et al.), the description of which is also incorporated herein by reference.

Example 1

Preparation of 5-Fluoro-1-methylsulfonoxy heptane (R)-6-benzyloxyhex-1-ene oxide was prepared by copper catalyzed addition of 3-benzyloxypropyl-1-magnesium bromide to R-epichlorohydrin to form R-1-chloro-6-benzyloxyhexan-2-ol which was then dehydrated under basic conditions to R-6-benzyloxyhex-1-ene oxide. This epoxide was then treated with methyl lithium (1.5 M in diethyl ether) in the presence of dilithiotetrachlorocuprate (0.02 molar equivalents, 0.1M in tetrahydrofuran) to yield S-1-benzyloxy-5-hydroxyheptane.

A dry one liter flask was equipped with an overhead stirrer, an addition funnel, and a thermocouple. S-1-benzyloxy-5-hydroxyheptane (11 g, 49.5 mmol) and 140 ml toluene were added to the flask under positive nitrogen pressure and cooled to −15° C. Perfluorobutanesulfonyl fluoride (26.3 g, 87.1 mmol) was then added to the cooled mixture. After about 5 minutes 1,8-diazobicyclo[5.4.0] undec-7-ene (DBU, 14 g, 92.1 mmol) was added at such a rate that the temperature did not rise above 5° C. After complete addition, the cooling bath was removed and the reaction mixture was stirred for one hour followed by addition of toluene (140 ml), then water (100 ml). The resultant upper toluene phase was washed with 100 ml 7% HCl, then with 2× 100 ml water. The toluene phase was evaporated under reduced pressure to yield 11.3 g of gold-colored liquid which was shown to be 84% of the desired R-1-benzyloxy-5-fluoroheptane and 13% olefin by gas chromatography. The crude product was further purified by chromatography on silica gel eluting with 40:1 v/v hexane/ethyl acetate to give 6.05 g of clear liquid; $^1$H-nmr showed this material to be 95% desired compound, 0.4% $RCH_2F$, 1.4% $RCH_2CF_2CF_2CF_2F$ and 3% ethyl ether (mole %).

The benzyl protecting group was removed by hydrogenation using 10% Pd on carbon. The resulting alcohol was treated with methanesulfonyl chloride in the presence of triethylamine to generate the desired intermediate R-5-Fluoro-1-methylsulfonoxy pentane.

Preparation of 5-hydroxy-2-[4-(6-(3-pentafluoroethoxy-2,2,3,3-tetrafluoropropoxy) hexyl)-phenyl]pyrimidine To a 1 liter round bottom flask fitted with an addition funnel, thermocouple and a mechanical stirrer was added 5-benzyloxy-2-[4-hydroxyphenyl]pyrimidine (20 g, 0.072 mol), perfluorobutanesufonyl fluoride (26.0, 0.086 mol) and t-butyl methyl ether (204 ml). The solution was cooled to 15° C., and DBU (13.1 g, 0.086 mol) was added through an addition funnel at a rate sufficient to maintain the reaction temperature below 30° C. The reaction was stirred for 2 hours at room temperature and then washed with water, 10% HCl and brine. The resulting organic layer was separated and concentrated. The product was recrystallized from ethanol to give 5-benzyloxy-2-[4-perfluorobutanesulfonoxyphenyl] pyrimidine.

To a 250 ml round bottom flask fitted with a magnetic stir bar and thermocouple was added 9-borabicylo[3.3.1]nonane (9-BBN, 53 ml of 0.5M soln in THF). The solution was stirred under a nitrogen atmosphere then cooled to 5° C. 3-pentafluoroethoxy-2,2,3,3-tetrafluoropropoxy)hex-6-ene (7.8 g, 0.022 mol, prepared from 1-bromohex-6-ene and 3-pentafluoroethoxy-2,2,3,3-tetrafluoropropanol) was added, and the mixture was stirred at room temperature for 4 hours. 5-benzyloxy-2-[4-perfluorobutanesulfonoxyphenyl]pyrimidine (10 g, 0.0195 mol), dichlorobis(triphenylphosphine) palladium II (0.27 g, 0.0004 mol), and sodium hydroxide (1.56 g, 0.039 mol) were added to the reaction mixture. The reaction was heated to 50° C. for 2 hours, cooled to room temperature, diluted with toluene (100 ml) and washed with water. The resulting organic phase was concentrated under reduced pressure, and the resulting product purified by column chromatography on silica gel using toluene as the eluent. The benzyl protecting group was then removed by hydrogenation using a 10% Pd on carbon catalyst to give 5-hydroxy-2-[4-(6-(3-pentafluoroethoxy-2,2,3,3-tetrafluoropropoxy)hexyl)-phenyl]pyrimidine.

Preparation of R-5-(5-fluoroheptyloxy)-2-[4-(6-(3-pentafluoroethoxy-2,2,3,3-tetrafluoropropoxy) hexyl)-phenyl]pyrimidine To a 100 ml round bottom flask was added a 1:1 solution of dimethylformamide and acetonitrile (50 ml), potassium carbonate (0.7 g, 5.1 mmol), 5-hydroxy-2-[4-(6-(3-pentafluoroethoxy-2,2,3,3-tetrafluoropropoxy)hexyl)-phenyl]pyrimidine (2.2 g, 4.24 mmol) and R-5-fluoro-1-methylsulfonoxy pentane (0.9 g, 4.24 mmol). The reaction mixture was heated to 80° C. for 16 hours and then cooled to room temperature. The solution was diluted with toluene (100 ml) and washed with water. The resulting organic phase was concentrated under reduced presssure, recrystallized from hexanes at −20° C. and further purified by column chromatography eluting with 10:1 v/v hexanes/ethyl acetate to yield 2.6 g of the desired product.

Example 2

Preparation of R-5-(5-fluorooctyloxy)-2-[4-(6-(3-pentafluoroethoxy-2,2,3,3-tetrafluoropropoxy) hexyl)-phenyl]pyrimidine This compound was prepared essentially as described in Example 1 except methyl lithium was replaced by ethyl magnesium bromide.

Example 3

Preparation of R-5-(6-fluoroheptyloxy)-2-[4-(6-(3-nonafluorobutoxy-2,2,3,3-tetrafluoropropoxy) hexyl)-phenyl]pyrimidine This compound was prepared essentially as described in Example 1 except methyl lithium was replaced by 4-benzyloxybutyl-1-magnesium bromide, the intermediate epoxide was reduced with lithium triethyl borohydride and 3-perfluorobutoxy-2,2,3,3-tetrafluoropropanol was used in place of 3-pentafluoroethoxy-2,2,3,3-tetrafluoropropanol.

Example 4

Preparation of 3-Fluoro-1-methylsulfonoxy hexane

This intermediate was prepared essentially as described in Example 1 using ethyl magnesium bromide and R-4- benzyloxy-1,2-epoxybutane (prepared essentially as described in J. A. Frick, Synthesis, vol. 7, pp. 621–3 (1992)).

Preparation of R-5-(3-fluorohexyloxy)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-phenyl]pyrimidine A 50 ml round bottom flask was charged with 5-hydroxy-2-[4-(4-(4-(1,2,2,3,3,4,4,4-nonafluorobutoxy)-1,1,2,2,3,3,4,4-octafluorobutoxy)2,2,3,3,4,4-hexaflurobutoxy)-phenyl]pyrimidine (2.0 g, 2.52 mmol prepared as described in U.S. Pat. No. 5,474,705), potassium carbonate (0.42 g, 3.0 mmol), dimethyl formamide (7.8 ml) and 3-fluoro-1-methylsulfonoxy hexane (0.55 g, 2.77 mmol). The reaction mixture was heated to 100° C. for 1 hour, then cooled to room temperature. The solution was diluted with 20 ml of toluene and then washed with water. The organic phase was isolated and concentrated under reduced pressure. The crude product was further purified by recrystalization from heptane, followed by and chromatography, eluting with 10:1 v/v hexane/ethyl acetate to give 1.13 g of the desired product.

Example 5

Preparation of (R)5-(4-fluorodecyloxy)-2-[4-(6-(2-pentafluoroethoxy-2,2-difluoroethoxy)hexyl)-phenyl]pyrimidine The title compound was prepared essentially as described in Example 1. R-4-fluoro-1-methanesulfonoxydecane was prepared by copper catalyzed addition of vinyl magnesium bromide to epichlorohydrin to yield 5-chloro-4-hydroxypent-1-ene which was treated with base to give the corresponding epoxide. The epoxide is then ring opened by the addition of propyl magnesium bromide to yield 4-hydroxy-dec-1-ene. This hydroxy compound is converted to 4-fluoro-dec-1-ene as described in Example 1, followed by treatment with borane/tetrahydrofuran and hydrogen peroxide to give 4-fluoro-decanol. This alcohol was treated with methane sulfonyl chloride in the presence of triethylamine to yield the desired intermediate R-4-fluoro-1-methylsulfonoxy decane.

Example 6

Preparation of R-5-(6-fluorooctyloxy)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-phenyl]pyrimidine The title compound was prepared essentially as described in Example 4 using R-6-fluoro-1-methylsulfonoxy octane (prepared from 7-benzyloxy-pent-1-ene oxide as described in Example 1) in place of R-3-fluoro-1-methylsulfonoxyhexane.

Example 7

Preparation of S-5-(6-fluoro-7-methoxy-heptyl)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-phenyl]pyrimidine The title compound was prepared essentially as described in Example 1 using 5-nonafluorobutoxysulfonoxy-2-[4-(4-(4-(1,1,2,2,3,3,4,4,4-nonafluorobutoxy)-1,1,2,2,3,3,4,4-octafluorobutoxy)2,2,3,3,4,4-hexafluorobutoxy)-phenyl]pyrimidine (prepared as described in Example 1) and S-6-fluoro-7-methoxy-hept-1-ene (prepared by addition of methanol to R-1,2-epoxyhept-1-ene and subsequent fluorination as described in Example 1).

Example 8

Preparation of R-5-(3-fluorohexyloxy)-2-[4-(6-(3-pentafluoroethoxy-2,2,3,3-tetrafluoropropoxy)hexyl)-phenyl]pyrimidine The title compound was prepared essentially as described in Example 1 using 3-fluoro-1-methansulfonoxyhexane (prepared as described in Example 4) in place of 5-fluoro-1-methanesulfonoxy-heptane.

Example 9

Preparation of R-5-(3-fluorohexyloxy)-2-[4-(6-(3-nonafluorobutoxy-2,2,3,3-tetrafluoropropoxy)hexyl)-phenyl]pyrimidine The title compound was prepared essentially as described in Example 1 using 3-fluoro-1-methansulfonoxyhexane (prepared as described in Example 4) in place of 5-fluoro-1-methanesulfonoxy-heptane and 3-nonafluorobutoxy-2,2,3,3-tetrafluoropropanol in place of 3-pentafluoroethoxy-2,2,3,3-tetrafluoropropanol (prepared as described in Example 1).

Example 10

Preparation of R-5-(3-fluorohexyloxy)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-3-fluorophenyl]pyrimidine The title compound was prepared essentially as described in Example 4 with the use of 5-benzyloxy-2-[3-fluoro-4-hydroxyphenyl]pyrimidine (prepared from 3-fluoro-4-hydroxybenzamidine hydrochloride and $(CH_3)_2NCH=(OCH_2C_6H_5)CHO$.

Example 11

Preparation of R-5-(3-fluorooctyloxy)-2-[4-(6-(3-pentafluoroethoxy-2,2,3,3-tetrafluoropropoxy)hexyl)-phenyl]pyrimidine The title compound was prepared essentially as described in Example 1 using 3-fluoro-1-methansulfonoxyoctane (prepared as described in Example 4 using butylmagnesium bromide) in place of 5-fluoro-1-methanesulfonoxy-heptane.

Example 12

Preparation of R-5-(3-fluorohexyloxy)-2-[4-(6-(3-pentafluoroethoxy-2,2,3,3-tetrafluoropropoxy)hexyl)-phenyl]pyrimidine The title compound was prepared essentially as described in Example 1 using 3-fluoro-1-methansulfonoxyoctane (prepared as described in Example 4 using butylmagnesium bromide) in place of 5-fluoro-1-methanesulfonoxy-heptane and 3-nonaflurobutoxy-2,2,3,3-tetrafluoropropanol in place of 3-pentafluoroethoxy-2,2,3,3-tetrafluoropropanol (prepared as described in Example 1).

Example 13

Preparation of R-5-(5-fluorohexyloxy)-2-[4-(6-(2-(2-(2-pentafluoroethoxy)-2,2,3,3-tetrafluoroethoxy)-2,2-difluoroethoxy)hexyl)-phenyl]pyrimidine The title compound was prepared essentially as described in Example 1 using 5-fluoro-1-methanesulfonoxyhexane in place of 5-fluoro-1-methanesulfonoxy-heptane and 2-(2-(2-pentafluoroethoxy)-2,2,3,3-tetrafluoroethoxy)-2,2-difluoroethan-1-ol in place of 3-pentafluoroethoxy-2,2,3,3-tetrafluoropropanol.

Example 14

Preparation of R-5-(5-fluorohexyloxy)-2-[4-(6-(3-pentafluoroethoxy-2,2,3,3-tetrafluoropropoxy)hexyl)-phenyl]pyrimidine The title compound was prepared essentially as described in Example 1 using 5-fluoro-1-methanesulfonoxyhexane in place of 5-fluoro-1-methanesulfonoxy-heptane.

Example 15

Preparation of R-5-(5-fluorohexyloxy)-2-[4-(6-(3-nonafluorobutoxy-2,2,3,3-tetrafluoropropoxy)hexyl)-phenyl]pyrimidine The title compound was prepared essentially as described in Example 3 using 5-fluoro-1-methanesulfonoxyhexane in place of 6-fluoro-1-methanesulfonoxy-heptane.

Example 16

Preparation of R-5-(5-fluoroheptyloxy)-2-[4-(6-(2-(2-(2-pentafluoroethoxy)-2,2,3,3-tetrafluoroethoxy)-2,2-difluoroethoxy)hexyl)-phenyl]pyrimidine The title compound was prepared essentially as described in Example 1 using 2-(2-(2-pentafluoroethoxy)-2,2,3,3-tetrafluoroethoxy)-2,2-difluoroethan-1-ol in place of 3-pentafluoroethoxy-2,2,3,3-tetrafluoropropanol.

Example 17

Preparation of R-5-(5-fluoroheptyloxy)-2-[4-(6-(3-nonafluorobutoxy-2,2,3,3-tetrafluoropropoxy)hexyl)-phenyl]pyrimidine The title compound was prepared essentially as described in Example 1 using 3-perfluorobutoxy-2,2,3,3-tetrafluoropropanol in place of 3-pentafluoroethoxy-2,2,3,3-tetrafluoropropanol.

Example 18

Preparation of R-5-(5-fluorooctyloxy)-2-[4-(6-(2-(2-(2-pentafluoroethoxy)-2,2,3,3-tetrafluoroethoxy)-2,2-difluoroethoxy)hexyl)-phenyl]pyrimidine The title compound was prepared essentially as described in Example 2 using 2-(2-2-pentafluoroethoxy)-2,2,3,3-tetrafluoroethoxy)-2,2-difluoroethan-1-ol in place of 3-pentafluoroethoxy-2,2,3,3-tetrafluoropropanol.

Example 19

Preparation of R-5-(5-fluoroheptyloxy)-2-[4-(6-(3-nonafluorobutoxy-2,2,3,3-tetrafluoropropoxy)hexyl)-phenyl]pyrimidine The title compound was prepared essentially as described in Example 2 using 3-perfluorobutoxy-2,2,3,3-tetrafluoropropanol in place of 3-pentafluoroethoxy-2,2,3,3-tetrafluoropropanol.

Example 20

Preparation of S-5-(6-fluorooctyl)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-phenyl]pyrimidine The title compound was prepared essentially as described in Example 7 using R-6-fluorooct-1-ene in place of S-6-fluoro-7-methoxy-hept-1-ene.

Example 21

Preparation of S-5-(6-fluorooctyl)-2-[4-(2-(2-(1,1,2,2,3,3,4,4,4-nonafluorobutoxy)-1,1,2,2-tetrafluoroethoxy)2,2-difluoroethoxy)-phenyl]pyrimidine The title compound was prepared essentially as described in Example 7 using R-6-fluorooct-1-ene in place of S-6-fluoro-7-methoxy-hept-1-ene and 5-nonafluorobutoxysulfonoxy-2-[4-(-(2-(2-(1,1,2,2,3,3,4,4,4-nonafluorobutoxy)-1,1,2,2-tetrafluoroethoxy)2,2-difluroethoxy)-phenyl]pyrimidine in place of 5-nonafluorobutoxysulfonoxy-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-phenyl]pyrimidine.

Example 22

Preparation of S-5-(6-fluorooctyl)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-3-fluorophenyl]pyrimidine The title compound was prepared essentially as described in Example 20 using 5-benzyloxy-2-[3-fluoro-4-hydroxyphenyl]pyrimidine(prepared from 3-fluoro-4-hydroxybenzamidine hydrochloride and $(CH_3)_2NCH=(OCH_2C_6H_5)CHO$) in place of 5-benzyloxy-2-[4-hydroxyphenyl]pyrimidine.

Example 23

Preparation of R-5-(6-fluorooctyloxy)-2-[4-(3-(2-(2-(2-trifluoromethoxy)-1,1,2,2-tetrafluoroethoxy)-1,1,2,2-tetrafluoroethoxy)2,2-difluoroethoxy)propyl)-phenyl]pyrimidine The title compound was prepared essentially as described in Example 1 with the use of R-6-fluoromethylsulfonoxy octane in place of 5-Fluoro-1-methylsulfonoxy heptane and 2-(2-(2-trifluoromethoxy)-1,1,2,2-tetrafluoroethoxy)-1,1,2,2-tetrafluoroethoxy)2,2-difluoroethoxy)prop-3-ene in place of 3-pentafluoroethoxy-2,2,3,3-tetrafluoropropoxy)hex-6-ene.

Example 24

Preparation of R-5-(6-fluorooctyloxy)-2-[4-(6-(3-pentafluoroethoxy)-2,2,3,3-tetrafluoropropoxy)hexyl)-phenyl]pyrimidine The title compound was prepared essentially as described in Example 1 with the use of R-6-fluoromethylsulfonoxy octane in place of 5-Fluoro-1-methylsulfonoxy heptane.

Example 25

Preparation of R-5-(6-fluorooctyloxy)-2-[4-(6-(3-perfluorobutoxy)-2,2,3,3-tetrafluoropropoxy)hexyl)-phenyl]pyrimidine The title compound was prepared essentially as described in Example 1 with the use of R-6-fluoromethylsulfonoxy octane in place of 5-Fluoro-1-methylsulfonoxy heptane 3-perfluorobutoxy-2,2,3,3-tetrafluoropropoxyhex-6-ene in place of 3-pentafluoroethoxy-2,2,3,3-tetrafluoropropoxy)hex-6-ene.

Example 26

Preparation of R-5-(6-fluorooctyloxy)-2-[4-(4-(4-(1,1,2,2,3,3,4,4,4-nonafluorobutoxy)-1,1,2,2,3,3,4,4-octafluorobutoxy)2,2,3,3,4,4-hexaflurobutoxy)-3-fluorophenyl]pyrimidine The title compound was prepared essentially as described in Example 6 using 5-benzyloxy-2-[3-fluoro-4-hydroxyphenyl]pyrimidine (prepared from 3-fluoro-4-hydroxybenzamidine hydrobromide and $(CH_3)_2NCH=C(OC_8H_{17})CHO$).

Preparation of Comparative Examples C-1 through C-6

Comparative Example 1

The compound was prepared essentially as described in Example 1 by combining 5-hydroxy-2-[4-(6-(2-(2-trifluoromethoxy)-tetrafluoroethoxy)-2,2,-difluoroethoxy)hexyl)-phenyl]pyrimidine (prepared essentially as described in Example 1 using 1-(2-(2-trifluoromethoxy)-tetrafluoroethoxy)-2,2,-difluoroethoxyhex-6-ene in place of 1-(3-pentafluoroethoxy-2,2,3,3-tetrafluoropropoxy)hex-6-ene) and R-2-fluoro-1-methylsulfonoxy octane (prepared from R-2-fluorooctan-1-ol and methylsulfonyl chloride) in place of 5-fluoro-1-methylsulfonoxy heptane.

Comparative Examples 2 and 3

These compounds were prepared essentially as described in Comparative Example 4 and Example 5, respectively, of U.S. Pat. No. 5,702,637.

Comparative Example 4

(R)5-Octyloxy-2-[4(7-(3-nonafluorobutoxy)-2,2,3,3-tetrafluoropropoxy)-6-fluoroheptyl)phenyl]pyrimidine The compound was prepared essentially as described in Example 1 with the substitution of R-(3-nonafluorobutoxy)-2,2,3,3-tetrafluoropropoxy 6-fluorohept-1-ene for 3-pentafluoroethoxy-2,2,3,3-tetrafluoropropoxy)hex-6-ene and substitution of 5-octyloxy-2-[4-hydroxyphenyl]pyrimidine] for 5-benzyloxy-2-[4-hydroxyphenyl]pyrimidine. R-(3-nonafluorobutoxy)-2,2,3,3-tetrafluoropropoxy 6-fluorohept-1-ene can be prepared by reaction of 1-butenyl-4-magnesium bromide and epichlorohydrin followed by addition of 3-nonafluorobutoxy-2,2,3,3-tetrafluoropropanol and subsequent fluorination as described in Example 1.

Comparative Example 5

(R)5-Hexyloxy-2-[4(7-(3-nonafluorobutoxy)-2,2,3,3-tetrafluoropropoxy)-7-fluorooctyl)phenyl]pyrimidine The compound was be prepared essentially as described in Example 1 with the substitution of R-(3-nonafluorobutoxy)-2,2,3,3-tetrafluoropropoxy -7-fluorooct-1-ene for 3-pentafluoroethoxy-2,2,3,3-tetrafluoropropoxy)hex-6-ene and substitution of 5-hexyloxy-2-[4-hydroxyphenyl]pyrimidine] for 5-benzyloxy-2-[4-hydroxyphenyl]pyrimidine. R-(3-nonafluorobutoxy)-2,2,3,3-tetrafluoropropoxy 7-fluorooct-1-ene can be prepared by reaction of 1-pentenyl-5-magnesium bromide and epichlorohydrin followed by addition of 3-nonafluorobutoxy-2,2,3,3-tetrafluoropropanol and subsequent fluorination as described in Example 1.

Comparative Example 6

(R)5-Heptyloxy-2-[4(7-(3-nonafluorobutoxy)-2,2-difluoroethoxy)-7-fluorooctyl)phenyl]pyrimidine The compound was prepared essentially as described in example 1 with the substitution of R-(3-nonafluorobutoxy)-2,2-difluoroethoxy -7-fluorooct-1-ene for 3-pentafluoroethoxy-2,2,3,3-tetrafluoropropoxy)hex-6-ene and substitution of 5-heptyloxy-2-[4-hydroxyphenyl]pyrimidine] for 5-benzyloxy-2-[4-hydroxyphenyl]pyrimidine. R-(3-nonafluorobutoxy)-2,2-difluoroethoxy 7-fluorooct-1-ene can be prepared by reaction of 1-pentenyl-5-magnesium bromide and epichlorohydrin followed by addition of 3-nonafluorobutoxy-2,2-difluoroethanol and subsequent fluorination as described in Example 1.

TABLE 1

Mesomorphic Phase Transitions (° C.)

| Example | Structure | I-Sa | to Sc | to Sm | to K | to Sc |
|---------|-----------|------|-------|-------|------|-------|
| 1 | (CH$_2$)$_6$OCH$_2$CF$_2$CF$_2$OC$_2$F$_5$ phenyl-pyrimidine-O-CH(F)-alkyl | 96 | 57 | 9 | −10 | 18 |
| 2 | (CH$_2$)$_6$OCH$_2$CF$_2$CF$_2$OC$_2$F$_5$ phenyl-pyrimidine-O-alkyl-CH(F) | 98 | 73 | 1 | −9 | 9 |
| 3 | (CH$_2$)$_6$OCH$_2$C$_2$F$_4$OC$_4$H$_9$ phenyl-pyrimidine-O-CH(F)-alkyl | 105 | 79 | −11 | | −8 |
| 4 | OCH$_2$C$_3$F$_6$OC$_4$F$_8$OC$_4$F$_9$ phenyl-pyrimidine-O-alkyl-CH(F) | 141 | 89 | 43 | | 49 |
| 5 | (CH$_2$)$_6$OCH$_2$CF$_2$CF$_2$OC$_2$F$_5$ phenyl-pyridine-alkyl-CH(F) | 81 | 72 | 17 | | 32 |
| 6 | OCH$_2$C$_3$F$_6$OC$_4$F$_8$OC$_4$F$_9$ phenyl-pyrimidine-O-alkyl-CH(F) | 130 | 97 | 53 | | 63 |
| 7 | OCH$_2$C$_3$F$_6$OC$_4$F$_8$OC$_4$F$_9$ phenyl-pyrimidine-alkyl-CH(F)-CH$_2$OCH$_3$ | 111 | 72 | 10 | | 31 |

TABLE 1-continued

| Example | Structure | Mesomorphic Phase Transitions (° C.) | | | | |
|---|---|---|---|---|---|---|
| | | I-Sa | to Sc | to Sm | to K | to Sc |
| 8 | pyrimidine-phenyl with $F$-chiral chain and $(CH_2)_6OCH_2C_2F_4OC_2F_5$ | 91.5 | | -31 | | -10 |
| 9 | pyrimidine-phenyl with $F$-chiral chain and $(CH_2)_6OCH_2C_2F_4OC_4F_9$ | 100 | 50 | -25 | | -14 |
| 10 | pyrimidine-(F-phenyl) with $F$-chiral chain and $OCH_2C_3F_6OC_4F_8OC_4F_9$ | 123 | 78 | 36.2 | | 43.3 |
| 11 | pyrimidine-phenyl with $F$-chiral chain and $(CH_2)_6OCH_2C_2F_4OC_4F_5$ | 95 | 64 | -3 | | 10 |
| 12 | pyrimidine-phenyl with $F$-chiral chain and $(CH_2)_6OCH_2C_2F_4OC_4F_9$ | 102 | 78 | 0 | | 10 |
| 13 | pyrimidine-phenyl with $F$-chiral chain and $(CH_2)_6OCH_2CF_2OC_2F_4OC_4F_5$ | 103 | 49 | -7 | -22 | 5 |

TABLE 1-continued

Mesomorphic Phase Transitions (° C.)

| Example | Structure | I-Sa | to Sc | to Sm | to K | to Sc |
|---|---|---|---|---|---|---|
| 14 | [structure with (CH$_2$)$_6$OCH$_2$C$_2$F$_4$OC$_2$F$_5$] | 96 | 22 | −7 | | 5 |
| 15 | [structure with (CH$_2$)$_6$OCH$_2$C$_2$F$_4$OC$_4$F$_9$] | 103 | 57 | −4 | | 7 |
| 16 | [structure with (CH$_2$)$_6$OCH$_2$CF$_2$OC$_2$F$_4$OC$_2$F$_5$] | 102 | 69 | 6 | | 15 |
| 17 | [structure with (CH$_2$)$_6$OCH$_2$C$_2$F$_4$OC$_4$F$_9$] | 103 | 73 | 10 | | 18 |
| 18 | [structure with (CH$_2$)$_6$OCH$_2$CF$_2$OC$_2$F$_4$OC$_2$F$_5$] | 104 | 82 | 1.3 | | 9 |
| 19 | [structure with (CH$_2$)$_6$OCH$_2$C$_2$F$_4$OC$_4$F$_9$] | 104 | 84 | 0 | | 5 |
| 20 | [structure with OCH$_2$C$_3$F$_6$OC$_4$F$_8$OC$_4$F$_9$] | 114 | 57 | 39 | −37 | 48 |

TABLE 1-continued

Mesomorphic Phase Transitions (° C.)

| Example | Structure | I-Sa | to Sc | to Sm | to K | to Sc |
|---|---|---|---|---|---|---|
| 21 | 4-(5-((S)-2-fluorohexyl)pyridin-2-yl)phenyl OCH$_2$CF$_2$OC$_2$F$_4$OC$_4$F$_9$ | 84 | 46 | 27 | | 44 |
| 22 | 4-(5-((S)-2-fluorohexyl)pyridin-2-yl)phenyl OCH$_2$C$_3$F$_6$OC$_4$F$_8$OC$_4$F$_9$ | 93 | 52 | 24 | | 36 |
| 23 | 4-(5-((S)-6-fluorohexyloxy)pyridin-2-yl)phenyl (CH$_2$)$_3$OCH$_2$CF$_2$OC$_2$F$_4$OC$_2$F$_4$OCF$_3$ | 118 | 83 | −11 | | −1 |
| 24 | 4-(5-((S)-6-fluorohexyloxy)pyridin-2-yl)phenyl (CH$_2$)$_6$OCH$_2$C$_2$F$_4$OC$_2$F$_5$ | 97 | 79 | −8 | | 1 |
| 25 | 4-(5-((S)-6-fluorohexyloxy)pyridin-2-yl)phenyl (CH$_2$)$_6$OCH$_2$C$_2$F$_4$OC$_4$F$_9$ | 105 | 88 | −7 | | 2 |
| 26 | 4-(5-((S)-6-fluorohexyloxy)pyridin-2-yl)phenyl OCH$_2$C$_3$F$_6$OC$_4$F$_8$OC$_4$F$_9$ | 107 | 88 | 56 | | 66 |
| C-1 | 4-(5-((S)-2-fluorooctyloxy)pyridin-2-yl)phenyl (CH$_2$)$_6$OCH$_2$CF$_2$OC$_2$F$_4$OCF$_3$ | I to Sc | 68.7 | 44.2 | 11.9 | 52.8 |

TABLE 1-continued

Mesomorphic Phase Transitions (° C.)

| Example | Structure | I-Sa | to Sc | to Sm | to K | to Sc |
|---|---|---|---|---|---|---|
| C-2 | [structure with pyrimidine, phenyl, OCH$_2$CF$_2$OC$_2$F$_4$OC$_4$F$_9$ and chiral fluoro alkyl chain] | 99 | 71 | 60 | | 73 |
| C-3 | [structure with pyrimidine, phenyl, OCH$_2$CF$_2$OC$_2$F$_4$OC$_4$F$_9$ and chiral fluoro alkyl chain] | 91 | 64 | −7 | | 43 |
| C-4 | C$_8$H$_{17}$O—[pyrimidine]—[phenyl]—(CH$_2$)$_5$—CHF—CH$_2$—OCH$_2$CF$_2$OC$_4$F$_9$ | 105 | 63 | −15 | | 22 |
| C-5 | C$_6$H$_{13}$O—[pyrimidine]—[phenyl]—(CH$_2$)$_6$—CHF—CH$_2$—OCH$_2$CF$_2$OC$_4$F$_9$ | 97 | 68 | −3 | | 14 |
| C-6 | C$_7$H$_{15}$O—[pyrimidine]—[phenyl]—(CH$_2$)$_6$—CHF—CH$_2$—OCH$_2$CF$_2$OC$_4$F$_9$ | 91 | 67 | 1 | | 13 |

The data of Table 1 shows that the compounds of the invention have broader mesomorphic temperature ranges for device use from −10° to 80° C. and are more stable in these phases at lower temperatures than the compounds of Comparative Examples 1 and 2. In comparison with the compounds of Comparative Examples 3–6, the compounds of the invention have similar mesomorphic temperature ranges for device use from −10° to 80° C.

Examples 27 to 32 and Comparative Examples C-7 to C-11

A series of devices, each containing a chiral compound of this invention or a comparative compound, were prepared essentially as described in U.S. Pat. No. 5,377,033 (Radcliffe). The ITO-constituted electrodes of each device were connected to a function generator with variable output voltage. The device was first heated to the isotropic temperatures and then cooled to the reduced temperature (T-$T_{A-C}$, the temperature below the SmA to SmC transition temperature) noted in Table 2 (below). The polarization (nC/cm$^2$) and the $\tau_{electric}$ were determined as described below:

The polarization of the devices were determined essentially as described by Miyasato et al. in Jap. J. Appl. Phys. 22, 661 (1983). The electronic response time, $\tau_{electric}$, was derived from the displacement current of the ferroelectric liquid crystal device under an applied square voltage pulse. The current was viewed on a 100 megahertz bandwidth oscilloscope. The usual decaying exponential, associated with a dielectric filled capacitor, was followed by the spontaneous polarization ($P_s$) switching pulse. The time from the rising edge of the voltage pulse to the peak of the $P_s$ pulse was taken to be $\tau_{electric}$. In these Examples subphases of the chiral tilted smectic mesophases, such as antiferroelectric or ferrielectric phases, were not specified.

TABLE 2

| Example | Compound from: | T-$T_{A-C}$ (° C.) | Ps (nC/cm$^2$) | TAU (μsec) |
|---|---|---|---|---|
| 27a | Ex 1 | −7 | 13.4 | 11.1 |
| 27b | " | −37 | 29.9 | 25.7 |
| 28a | Ex 2 | −22 | 13.4 | 15 |
| 29a | Ex 3 | −28 | 26.8 | 11.7 |
| 29a | " | −58 | 45.8 | 25.3 |
| 30a | Ex 4 | −10 | 24.4 | 8.8 |
| 30a | " | −39 | 48 | 17.5 |
| 31a | Ex 5 | −11 | −14.2 | 11.1 |
| 31b | " | −36 | 18 | 28.7 |
| 32a | Ex 8 | −10 | * | 18.1 |
| 32b | " | −20 | * | 25.7 |
| C-7a | C-1 | −10 | 89 | 7.5 |
| C-7b | " | −20 | 113 | 8.9 |
| C-8a | C-2 | −4 | 53 | 10.4 |
| C-9a | C-3 | −14 | 103 | 5.0 |
| C-9b | " | −34 | 139 | 8.8 |
| C-10a | C-4 | −20 | 14 | 14 |
| C-10b | " | −40 | 18 | 27 |
| C-11a | C-5 | −20 | 26 | 8 |
| C-11b | " | −40 | 38 | 13 |

*Unable to measure under standard conditions

The results in Table 2 show that the compounds of Comparative Examples C-7, C-8 and C-9 had large polarization values (typically greater than 100 nC/cm2 below $T_{A-C}$−20) in comparison to the compounds of the invention (typically less than 50 nC/cm$^2$ below $T_{A-C}$−20). Low polarization values are important for the practical operation of a liquid crystal device. Polarization reversal fields, which cause switching or partial switching back to a material's original director alignment, are larger for higher polarization liquid crystal compounds or mixtures. This polarization reversal results in loss of the bistability that is crucial to the passive-matrix driving of ferroelectric liquid crystal devices. Another potential disadvantage of using high polarization mixtures is the partial switching of director alignment in response to non-switching (secondary) signals in a driving waveform. This continued response or fluctuation of the director causes a large decrease in the contrast ratio of a ferroelectric liquid crystal device. This indicates that these comparative materials should be diluted with achiral materials in order to reduce the polarization of the mixtures.

The compounds of the invention show similar polarization values and response times in comparison with the compounds of Comparative Examples C-10 and C-11. However, the compounds of the invention allow much easier synthetic variation of the terminal portion comprising the extended group, than the compounds of the Comparative Examples (where the compounds have a chiral, extended fluorochemical terminal). Structural changes in this portion of the molecule have large effects on mesomorphic transition temperatures, tilt angles, and other properties. The benefits and effects of changing this portion of the molecule have been described Applicant's U.S. Ser. No. 08/827,753 and U.S. Ser. No. 08/827,287.

Further, as can be seen in Table 2, the compounds of this invention had a high temperature dependence of the polarization $P_s$. An increase in the temperature dependence of the polarization results in a decrease in the temperature dependence of $\tau_{electric}$.

Surprisingly, Example 31a,b of Table 2 exhibited a polarization behavior (nC/cm$^2$) that inverted with a decrease in temperature (° C.) from the Smectic A mesophase to the Smectic C mesophase. FIG. 1 (below) shows the change in polarization for Examples 27a,b and 31a,b of the invention and demonstrates a change from a negative to a positive polarization value for Example 31 of the current invention. This enables the formulation of mixtures with temperature independent switching as shown in Example 36(below).

Examples 33 to 35 and Comparative Examples C-12 to C-13

When the $\tau_{electric}$ (switching time) and temperature data in Table 2 is plotted as the ln($\tau_{electric}$) versus temperature, relatively small changes in response times are observed over the temperature ranges, demonstrating that the liquid crystal compounds of the invention have the desirable property of reduced temperature dependent switching; this data is tabulated below in Table 4, as the slope (change in ln($\tau_{electric}$)/ change in temperature) along with the average polarization and average temperature of the range. For comparative purposes, examples from U.S. Pat. No. 5,262,388 and U.S. Pat. No. 5,702,637 are included in Table 4. In Table 4 Tc−10 to Tc−40 refers to the temperature range from −10° C. to −40° C. below the Smectic A to Smectic C transition temperature. Comparative Example 13 is a mixture disclosed in Example 36 of U.S. Pat. No. 5,702,637 (Johnson et al.). Shown below in Tables 3 and 4 are the compounds used and the weight percents used in preparing the mixture of this Comparative Example.

TABLE 3

| Example | Compound | Reference | Weight % |
|---------|----------|-----------|----------|
| C-13 | $C_8H_{17}$—[pyrimidine]—[phenyl]—$OCH_2CFH*CH_2OC_2F_4OC_2F_4OC_4F_9$ | Ex 36 US 5702637 | 9.7 |
| | $C_8H_{17}O$—[pyrimidine]—[phenyl]—$OCH_2CF_2OC_2F_4OC_4F_9$ | | 11.5 |
| | $C_{10}H_{21}O$—[pyrimidine]—[phenyl]—$OCH_2C_3F_6OC_4F_8OC_4F_9$ | | 11.6 |
| | $C_{10}H_{21}O$—[pyrimidine]—[phenyl]—$OCH_2CF_2OC_2F_4OC_6F_{13}$ | | 12.6 |
| | $C_8H_{17}$—[pyrimidine]—[phenyl]—$OCH_2CF_2OC_2F_4OC_4F_9$ | | 6.6 |
| | $C_8H_{17}$—[pyrimidine]—[phenyl]—$OCH_2C_3F_6OC_4F_8OC_4F_9$ | | 13.4 |
| | $C_{10}H_{21}$—[pyrimidine]—[phenyl]—$OCH_2C_3F_6OC_4F_8OC_4F_9$ | | 34.7 |

TABLE 4

Temperature dependence of switching over temperature range of Tc-10 to Tc-40

| Example | Compound from: | Slope | average Ps (nC/cm$^2$) | average Temp (° C.) |
|---------|----------------|-------|------------------------|---------------------|
| 33 | Ex 1 | −.028 | 22 | 35 |
| 34 | Ex 2 | −.017 | 17 | 44 |
| 35 | Ex 3 | −.018 | 24 | 56 |
| C-12 | C-3 | −.029 | 127 | 35 |
| C-13 | Table 3 | −.038 | 11 | 45 |

The data in Table 4 shows that similar, and in some cases, less temperature dependant-switching behavior was obtained with compounds of the invention relative to the compounds and composition of Comparative Examples C-12 and C-13. The compounds of Comparative Example C-13 illustrates the effect on the temperature dependence of switching by diluting a high polarization material with achiral compounds. In this comparison, Comparative Example C-12 provided good temperature dependence of switching when used at 100 wt. %, but it had a polarization that was too high for some device applications. Upon diluting this compound with achiral materials, the polarization was lowered to the range of compounds of the invention, however, the temperature dependency of switching increased dramatically.

Example 36

In the following Example, a device was prepared as described in Example 27 and filled with the mixture shown in Table 5. The temperature dependence of Tau ($\tau_{electric}$, switching time in $\mu$sec) was evaluated from $T_{A-C}$−10° C. to $T_{A-C}$−40° C. (the temperature range below the Smectic A to Smectic C transition temperature) by analysis of the change in(ln tau)/$\Delta$T(in degrees Centigrade below the Smectic A to Smectic C transition). Shown below in Table 5 are the compounds and the weight percents used to prepare the mixture of this Example along with the slope values. Also in FIG. 2 (below) the polarization vs. temperature of the mixture is plotted for the mixture and its constituent compounds. In Table 2 polarization values are in nC/cm$^2$ and temperature is in °C.

TABLE 5

| Example | Compound | Reference | Weight % | Tau slope |
|---------|----------|-----------|----------|-----------|
| 36 | [structure: CH₃(CH₂)₅CHF(CH₂)₃O-pyridine-phenyl-(CH₂)₆OCH₂CF₂OC₂F₅] | Ex 5 | 50 | −0.007 |
|  | [structure: C₈H₁₇O-pyridine-phenyl-(CH₂)₅CHF-OCH₂C₂F₄OC₄F₉] | C-4 | 25 |  |
|  | [structure: C₇H₁₅O-pyridine-phenyl-(CH₂)₆CHF-OCH₂CF₂OC₄F₉] | C-6 | 25 |  |

Figure 2:
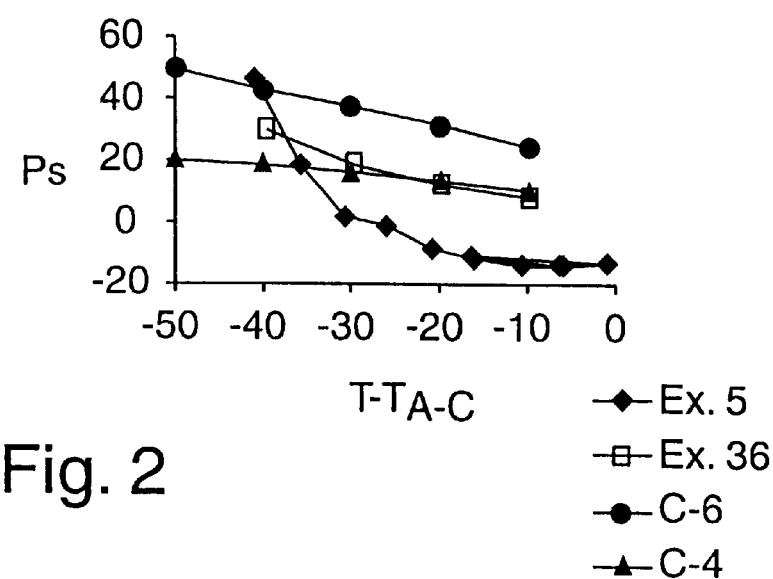
Figure 3:
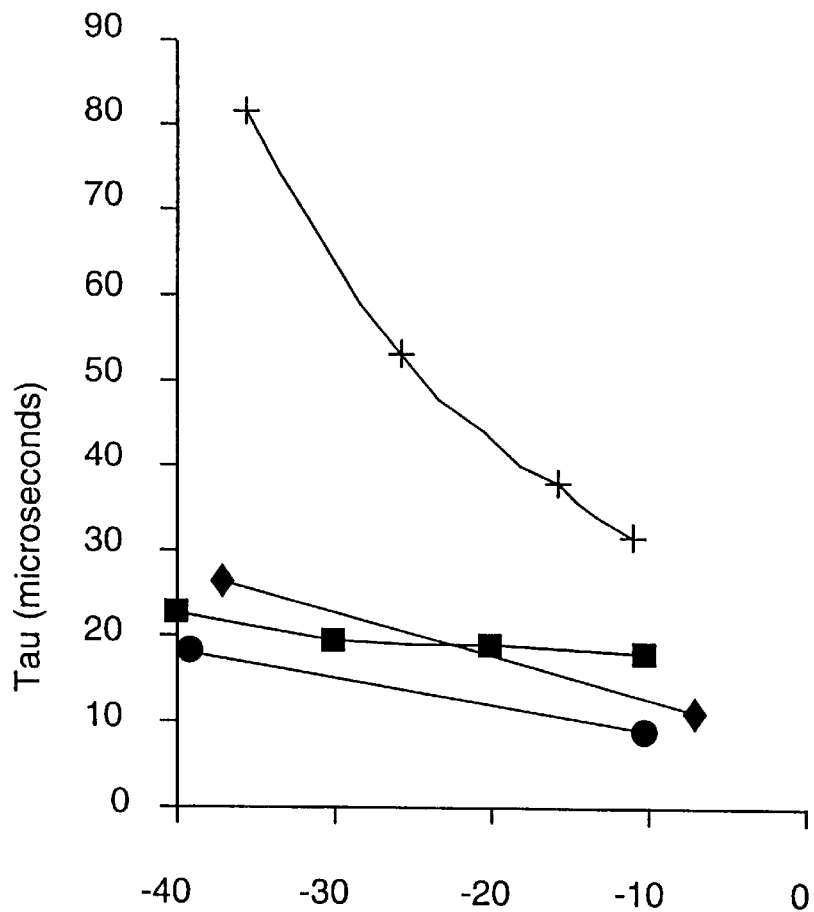
FIG. 3 show the temperature dependence of the switching speed $\tau_{electric}$ of the compounds of the invention.

As can be seen in Table 5 and FIG. 2, the mixing of a material which has a negative to positive polarization inversion effect (on cooling) with materials which have positive polarization led to a mixture with a decreased temperature dependence of switching (FIG. 3). Conversely the mixing of a material which has a positive to negative polarization inversion effect (on cooling) with materials which have negative polarization can also lead to a mixture with a decreased temperature dependence of switching. In these cases the resultant mixture has an increased temperature dependence of polarization, which leads to a decreased temperature dependence of the switching properties.

When the tau electric (switching time) and temperature data in Table 2 is plotted as the $\tau_{electric}$ versus temperature as shown in FIG. 3, relatively small changes in response times are observed over the temperature ranges, demonstrating that the liquid crystal materials of the this invention have the desirable property of reduced temperature dependent switching; this data is tabulated above in Table 4, as the slope (change in ln(tau electric )/(change in temperature) along with the average polarization and average temperature of the range. For comparative purposes examples from U.S. Pat. Nos. 5,262,388 and 5,702,637 are included in Table 3 Comparative Example 13 is a mixture disclosed in Example 36 of U.S. Pat. No. 5,702,637 (Johnson et al.).

Example 37

A cell of the type described in U.S. Pat. No. 5,377,033 (Radcliffe) was filled with the compound of Example 6 and placed in a hot stage with openings to allow transmitted light. The hot stage and the cell were placed between the crossed polarizers of a transmitting, polarizing microscope. The microscope was equipped with a HAMAMATSU Model HC 124-01 photomultiplier tube (PMT) and amplifier to detect the transmitted light levels. The PMT amplifier output was connected to a TEKTRONIX Model TDS 420 oscilloscope. A triangle waveform test signal was generated by a WAVETEK Model 395 arbitrary function generator. The signal from the generator was amplified through a Krone-Hite Model 7602 wideband amplifier. The oscilloscope was set to plot the transmission signal versus the triangle waveform test signal. The cell was heated to about 10 degrees above the isotropic transition of the liquid crystal composition and was cooled back down at 0.5 degrees per minute to the smectic A phase, without any signal being applied to the cell.

The microscope stage was rotated to align a zero field optical axis (smectic layer normal) of the liquid crystal composition with one of the crossed polarizers. The cell was cooled to a few degrees above a tilted smectic phase of the liquid crystal composition. To enable the tilted phase to be detected, the triangle signal was applied to the cell. A phase change (at $T_{A-C}$) from the smectic A mesophase to the tilted smectic mesophase was detected by a change in transmission signal to a non-linear response. In a smectic A mesophase, any transmission signal from the PMT is due to an electroclinic effect which gives a domainless, linear transmission response. In a tilted smectic or induced tilted smectic mesophase, the transmission response becomes non-linear. Transmission versus voltage curves were generated at selected frequencies and selected temperatures, (80° C. and 90° C., indicated in FIGS. 4 and 5 below, repectively).

Figure 4:
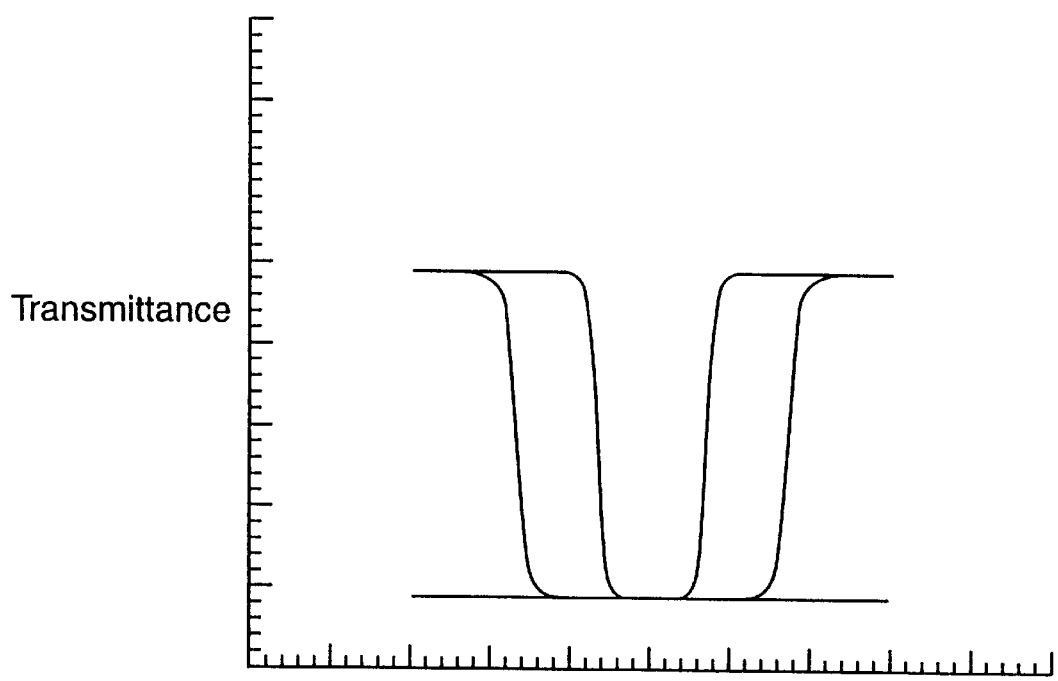
FIGS. 4 and 5 show tristable switching behavior of selected compounds of the invention.
Figure 5:
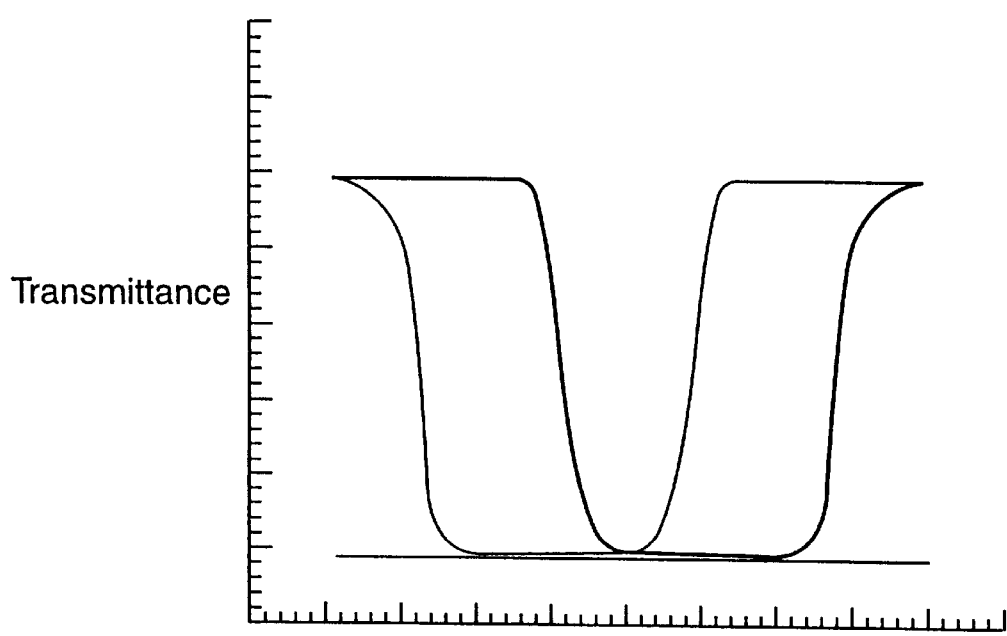

As can be seen in FIGS. 4 and 5, the compound of this Example exhibited tristable switching, a distinct threshold, a double hysteresis allowing for a memory effect in either of the driven states, and was easily switched to produce a device having few defects and allowing for the recovery of alignment The micro-second switching speed observed for this compound is considerably faster than the millisecond switching speed of currently used nematic liquid crystal compounds.

Various modifications and alterations of this invention will become apparent to those skilled in the art without departing from the scope and spirit of this invention.

What is claimed is:
1. Fluorine containing, chiral liquid crystal compounds represented by the formula:

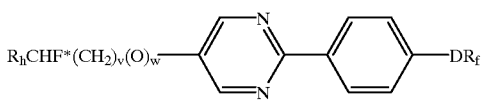

wherein:
D is non-directionally selected from the group consisting of a covalent bond,

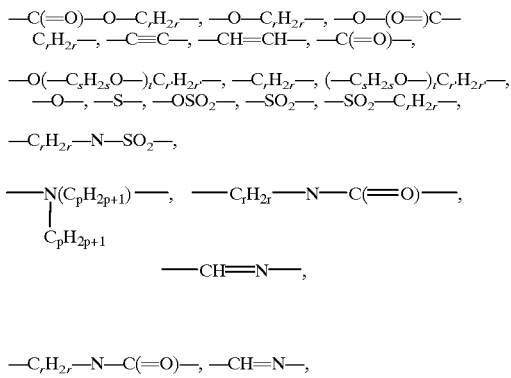

and combinations thereof;
$R_f$ is an achiral fluoroalkyl, perfluoroalkyl, fluoroether, or perfluoroether group;
r and r' are independently integers of 0 to about 20, s is independently an integer of 1 to about 10 for each $(C_sH_{2s}O)$, t is an integer of 1 to about 6, and p is an integer of 0 to about 4;
$R_h$ is a linear or branched alkyl group of 1 to about 10 carbon atoms;
—CHF*— represents a chiral center;
v is an integer of from 2 to about 10 and w is an integer of 0 or 1, with the proviso that v+w is at least 3;
where one or more non-adjacent —CH$_2$— groups may be replaced with an oxygen atom and where one or more ring hydrogen atoms can be replaced by fluorine atoms.

2. The compounds of claim 1 wherein said $R_f$ group is represented by the formula —$C_qF_{2q}X'$, where q is an integer of 1 to about 20 and X' is hydrogen or fluorine.

3. The compounds of claim 1 wherein $R_f$ is represented by the formula —$(C_xF_{2x}O)_zC_yF_{2y+1}$, where x is independently an integer of 1 to about 12 for each $(C_xF_{2x}O)$, y is an integer of 1 to about 12, and z is an integer of 1 to about 10.

4. The compounds of claim 3 wherein x is independently an integer of 1 to about 6 for each $(C_xF_{2x}O)$, y is an integer of 1 to about 6, and z is an integer of 1 to about 6.

5. A mixture of liquid crystal compounds comprising at least one compound of claim 1.

6. The mixture of claim 5 further comprising at least one other liquid crystal compound having at least one fluorinated terminal portion.

7. The compounds of claim 1 wherein the slope of the plot of $\Delta(\ln \tau_{electric})/\Delta T$ is greater than $-0.03$.

8. The compounds of claim 1 wherein the polarization ($P_s$) value of said compounds switch from positive to negative (+ to −), or negative to positive (− to +) as the temperature is reduced from the smectic A to smectic C transition temperature.

9. A liquid crystal device containing at least one compound of claim 1.

10. The device of claim 9 wherein said compound has a polarization ($P_s$) of less than about 100 nC/cm$^2$ at the operating temperature of said device.

11. The device of claim 9 wherein the polarization ($P_s$) value of said compound switches from positive to negative (+ to −), or negative to positive (− to +) as the temperature is reduced from the smectic A to smectic C transition temperature.

12. A tristable liquid crystal device containing at least one compound of claim 1.

13. A tristable liquid crystal device comprising (a) first and second opposed substrates, at least one of said substrates bearing an alignment coating, and each said substrate bearing at least one electrode so as to define one or a plurality of pixels; (b) a tilted smectic or induced tilted smectic liquid crystal composition disposed between said substrates; and (c) a pair of orthogonally disposed polarizers, each having a polarization axis, one said polarization axis being aligned with the zero field optical axis of a tilted smectic or induced tilted smectic mesophase of said liquid crystal composition; wherein said substrates are disposed so as to provide an alignment of said liquid crystal composition, said composition comprising at least one chiral liquid crystal compound represented by the following formula:

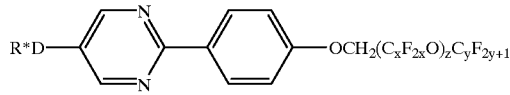

where:
R* is a saturated or unsaturated chiral hydrocarbon or hydrocarbon ether moiety containing at least one chiral center;
D is non-directionally selected from the group consisting of a covalent bond,

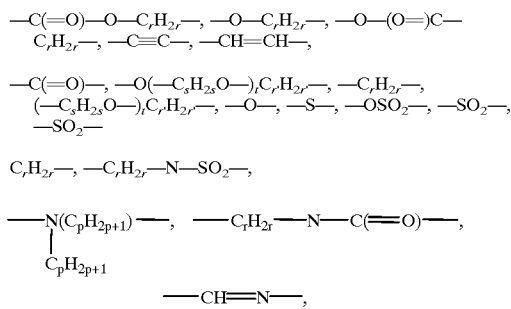

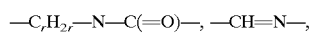

and combinations thereof, where r and r' are independently integers of 0 to about 20, s is independently an integer of 1 to about 10 for each $(C_sH_{2s}O)$, t is an integer of 1 to about 6, and p is an integer of 0 to about 4;
x is independently an integer of 1 to about 12 for each $(C_xF_{2x}O)$;
y is an integer of 1 to about 12; and
z is an integer of 1 to about 10 and where one or more ring hydrogen atoms can be replaced with fluorine atoms, and where one or more ring hydrogen atoms can be replaced by fluorine atoms.

14. A process for reducing the temperature dependence of the response time of a liquid crystal mixture which comprises the step of combining:

(a) at least one compound comprising (i) an achiral fluorochemical terminal portion which comprises a terminal fluoroalkyl, fluoroether, perfluoroalkyl, or perfluoroether group; (ii) a chiral terminal portion comprising a chiral hydrocarbon or chiral hydrocarbon ether group comprising a chiral center and (iii) a central core connecting said terminal portions; said chiral terminal portion having at least three in-chain atoms between said chiral center and said central core; with (b) at least one other liquid crystal composition comprising at least one smectic or latent smectic liquid crystal compound having a temperature dependent switching when in a device.

15. The process of claim 14 wherein said compound (b) having a temperature dependent switching has a slope more negative than −0.02.

* * * * *

UNITED STATES PATENT AND TRADEMARK OFFICE
CERTIFICATE OF CORRECTION

PATENT NO.  : 6,139,924
DATED       : October 31, 2000
INVENTOR(S) : Michael P. Keyes et al.

It is certified that error appears in the above-identified patent and that said Letters Patent is hereby corrected as shown below:

Column 6,
Line 45, delete the second occurrence of "—$OSO_2$—, —$SO_2$—, —$SO_2$—$C_rH_{2r}$—,".

Column 24,
Example 6, the structure, should read 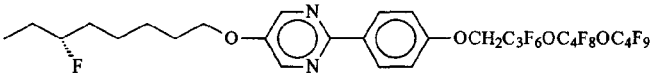

Column 29,
Example 23, the structure, 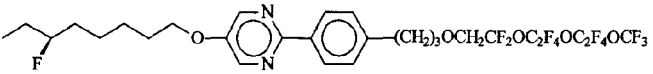

should read 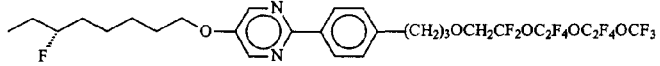

Column 30,
Example 24, the structure, 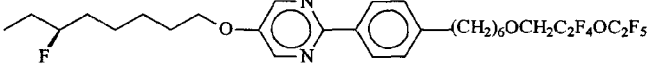

should read 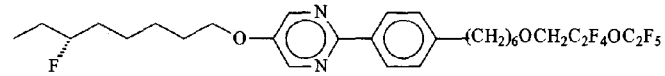

Example 25, the structure, 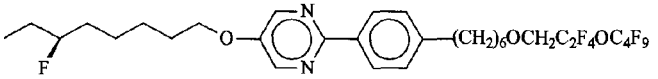

should read 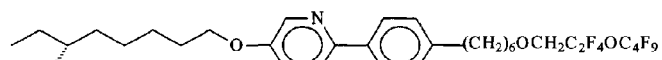

Example 26, the structure, 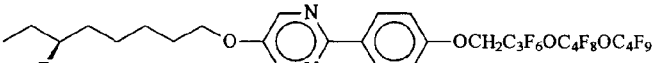

should read 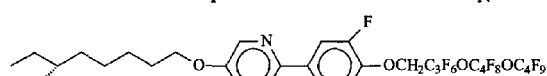

UNITED STATES PATENT AND TRADEMARK OFFICE
CERTIFICATE OF CORRECTION

PATENT NO. : 6,139,924
DATED : October 31, 2000
INVENTOR(S) : Michael P. Keyes et al.

It is certified that error appears in the above-identified patent and that said Letters Patent is hereby corrected as shown below:

<u>Column 33,</u>
Line 65, delete "$T_{A-c}$-20)" and insert therefore -- $T_{A-C}$-20° --.
Line 66, delete "$T_{A-c}$-20)" and insert therefore -- $T_{A-C}$-20° --.

<u>Column 39,</u>
Line 24, delete the second occurrence of "—$C_rH_{2r}$—N—C(=O)—,—CH=N—,".

<u>Column 40,</u>
Line 55, delete the second occurrence of "—$C_rH_{2r}$—N—C(=O)—,—CH=N—,".

Signed and Sealed this

Sixteenth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,139,924
DATED         : October 31, 2000
INVENTOR(S)   : Keyes et al.

It is certified that error appears in the above-identified patent and that said Letters Patent is hereby corrected as shown below:

Column 3, line 62 through Column 4, line 10,
Please delete the structure and insert the following:

$-C(=O)-O-C_rH_{2r}-$, $-O-C_rH_{2r}-$, $-O-(O=)C-C_rH_{2r}-$, $-C\equiv C-$, $-CH=CH-$, $-C(=O)-$, $-O(C_sH_{2s}O)_tC_{r'}H_{2r'}-$, $-C_rH_{2r}-(C_sH_{2s}O)_tC_{r'}H_{2r'}-$, $-O-$, $-S-$, $-OSO_2-$, $-SO_2-$, $-SO_2-C_rH_{2r}-$,   $-C_rH_{2r}-\overset{C_pH_{2p+1}}{\underset{|}{N}}-SO_2-$,   $-N(C_pH_{2p+1})-$ $-C_rH_{2r}-\overset{C_pH_{2p+1}}{\underset{|}{N}}-C(=O)-$,   $-CH=N-$ Column 6, line 34 through line 51,
Please delete the structure ending in "...combinations thereof," and insert the following:

$-C(=O)-O-C_rH_{2r}-$, $-O-C_rH_{2r}-$, $-O-(O=)C-C_rH_{2r}-$, $-C\equiv C-$, $-CH=CH-$, $-C(=O)-$, $-O(C_sH_{2s}O)_tC_{r'}H_{2r'}-$, $-C_rH_{2r}-(C_sH_{2s}O)_tC_{r'}H_{2r'}-$, $-O-$, $-S-$, $-OSO_2-$, $-SO_2-$, $-SO_2-C_rH_{2r}-$,   $-C_rH_{2r}-\overset{C_pH_{2p+1}}{\underset{|}{N}}-SO_2-$,   $-N(C_pH_{2p+1})-$ $-C_rH_{2r}-\overset{C_pH_{2p+1}}{\underset{|}{N}}-C(=O)-$,   $-CH=N-$ and combinations thereof,

UNITED STATES PATENT AND TRADEMARK OFFICE
CERTIFICATE OF CORRECTION

PATENT NO. : 6,139,924
DATED : October 31, 2000
INVENTOR(S) : Keyes et al.

It is certified that error appears in the above-identified patent and that said Letters Patent is hereby corrected as shown below:

<u>Column 39, line 11 through line 25,</u>
Please delete the structure in claim 1 and insert the following:

$-C(=O)-O-C_rH_{2r}-$, $-O-C_rH_{2r}-$, $-O-(O=)C-C_rH_{2r}-$, $-C\equiv C-$, $-CH=CH-$,
$-C(=O)-$, $-O(C_sH_{2s}O)_tC_rH_{2r'}-$, $-C_rH_{2r}-(C_sH_{2s}O)_tC_{r'}H_{2r'}-$, $-O-$, $-S-$, $-OSO_2-$, $-SO_2-$, $$-SO_2-C_rH_{2r}-,\quad -C_rH_{2r}-\overset{C_pH_{2p+1}}{\underset{|}{N}}-SO_2-,\quad -N(C_pH_{2p+1})-$$

$$-C_rH_{2r}-\overset{C_pH_{2p+1}}{\underset{|}{N}}-C(=O)-,\quad -CH=N-$$

<u>Column 40, line 41 through line 55,</u>
Please delete the structure in claim 13 and insert the following:

$-C(=O)-O-C_rH_{2r}-$, $-O-C_rH_{2r}-$, $-O-(O=)C-C_rH_{2r}-$, $-C\equiv C-$, $-CH=CH-$,
$-C(=O)-$, $-O(C_sH_{2s}O)_tC_rH_{2r'}-$, $-C_rH_{2r}-(C_sH_{2s}O)_tC_{r'}H_{2r'}-$, $-O-$, $-S-$, $-OSO_2-$, $-SO_2-$, $$-SO_2-C_rH_{2r}-,\quad -C_rH_{2r}-\overset{C_pH_{2p+1}}{\underset{|}{N}}-SO_2-,\quad -N(C_pH_{2p+1})-$$

$$-C_rH_{2r}-\overset{C_pH_{2p+1}}{\underset{|}{N}}-C(=O)-\quad -CH=N-$$

Signed and Sealed this

Nineteenth Day of November, 2002

*Attest:*

*Attesting Officer*

JAMES E. ROGAN
*Director of the United States Patent and Trademark Office*